United States Patent [19]

Dininno et al.

[11] Patent Number: 5,132,421

[45] Date of Patent: * Jul. 21, 1992

[54] 2-NAPHTHYL-CARBAPENEM INTERMEDIATES

[75] Inventors: Frank P. Dininno, Old Bridge; Mark L. Greenlee, Rahway, both of N.J.

[73] Assignee: Merck & Co., Inc., Rahway, N.J.

[*] Notice: The portion of the term of this patent subsequent to Apr. 9, 2008 has been disclaimed.

[21] Appl. No.: 594,213

[22] Filed: Oct. 9, 1990

[51] Int. Cl.$^5$ .................. C07D 487/04; A61K 31/40; C07F 7/18
[52] U.S. Cl. ..................................................... 540/302
[58] Field of Search ........................ 540/302; 514/210

[56] References Cited

U.S. PATENT DOCUMENTS

| | | | |
|---|---|---|---|
| 4,260,627 | 4/1981 | Christensen et al. | 424/274 |
| 4,465,632 | 8/1984 | Christensen et al. | 260/245.2 |
| 4,543,257 | 9/1985 | Cama et al. | 514/210 |
| 4,775,669 | 10/1988 | Cama et al. | 514/210 |
| 4,962,101 | 10/1990 | DiNinno et al. | 514/210 |
| 4,988,703 | 1/1991 | Norbeck et al. | 514/262 |
| 5,003,099 | 3/1991 | Mettler et al. | 558/445 |
| 5,006,519 | 4/1991 | DiNinno et al. | 514/210 |
| 5,011,832 | 4/1991 | Dininno et al. | 514/210 |
| 5,011,848 | 4/1991 | Semeraro et al. | 514/356 |
| 5,015,260 | 5/1991 | Tamura et al. | 564/443 |
| 5,019,173 | 5/1991 | Gettings et al. | 134/4 |
| 5,023,250 | 6/1991 | Adams et al. | 514/179 |
| 5,026,869 | 6/1991 | Flaugh | 548/436 |
| 5,029,979 | 7/1991 | Robello et al. | 385/141 |

FOREIGN PATENT DOCUMENTS 0277743 10/1988 European Pat. Off. .

OTHER PUBLICATIONS

L. D. Cama et al., Total Synthesis of Thienamycin Analogs-III, Tetrahedron 39, 2531 (1983).
R. N. Guthikonda, et al., Structure Activity Relationships in the 2-Arylcarbapenem Series, J. Med. Chem., 30, 871 (1987).
Sumita, Y., et al., Eur. J. Clin. Microbiol. Infect. Dis., vol. 10, No. 2, p. 77 (1991).
Chambers H. F., Clin. Microbiol. Rev., vol. 1 (1988).

Primary Examiner—Mukund J. Shah
Assistant Examiner—Jyothsna Venkat
Attorney, Agent, or Firm—John W. Harbour; Hesna J. Pfeiffer

[57] ABSTRACT

Carbapenems of the formula

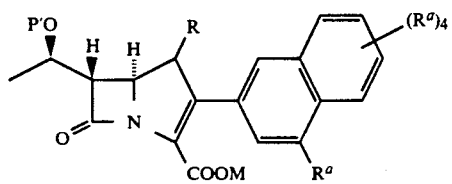

are useful intermediates to antibacterial agents.

4 Claims, No Drawings

2-NAPHTHYL-CARBAPENEM INTERMEDIATES

BACKGROUND OF THE INVENTION

The present invention relates to antibacterial agents of the carbapenem class, in which the 2-position sidechain is characterized by a naphthalene moiety, substituted by various neutral substituents, as described in more detail further below.

Thienamycin was an early carbapenem antibacterial agent having a broad spectrum; it has the following formula:

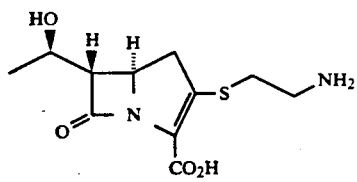

Later, N-formimidoyl thienamycin was discovered; it has the formula:

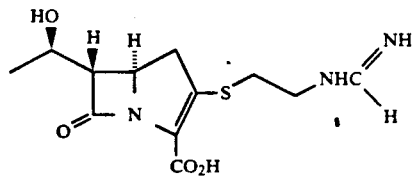

The 2-naphthyl-carbapenems of the present invention are not characterized by a broad antibacterial spectrum such as that of thienamycin or N-formimidoyl thienamycin. Rather, their spectrum of activity is largely limited to gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy of these difficult to control pathogens. Moreover, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount of resistance in the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

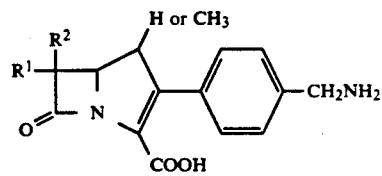

However, there is no description or suggestion of a substituted naphthyl 2-substituent such as characterizes the compounds of the present invention, nor is there any suggestion of the suprisingly better anti-MRSA/MRCNS activity of the compounds of the present invention.

EP-A-0277 743 describes a particular class of compounds of the formula:

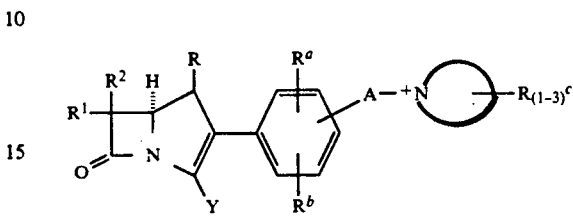

but this limited teaching in no way suggests the totally different compounds of the present invention, nor their surprisingly better anti-MRSA/MRCNS activity.

SUMMARY OF INVENTION

The present invention provides novel carbapenem compounds of the formula:

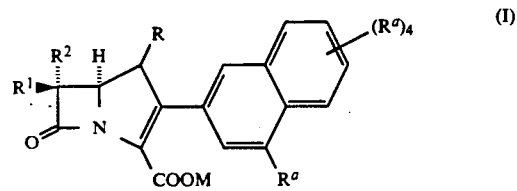

wherein:

R is H or $CH_3$;

$R^1$ and $R^2$ are independently H, $CH_3-$, $CH_3CH_2-$, $(CH_3)_2CH-$, $HOCH_2-$, $CH_3CH(OH)-$, $(CH_3)_2C(OH)-$, $FCH_2CH(OH)-$, $F_2CHCH(OH)-$, $F_3CCH(OH)-$, $CH_3CH(F)-$, $CH_3CF_2-$, or $(CH_3)_2C(F)-$;

$R^a$ are independently selected from the group consisting of hydrogen and the radicals set out below, provided that one but not more than one $R^a$ is selected from Type I substituents and zero to three $R^a$ radicals are selected from Type II substituents; wherein the Type I substituents are:

I. a)

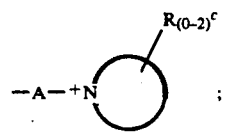

where

A is $(CH_2)_m-Q-(CH_2)_n$, where m is 0 to 6 and n is 1 to 6 and Q is a covalent bond, O, S, SO, $SO_2$, NH, $-SO_2NH-$, $-NHSO_2-$, $-CONH-$, $-NHCO-$, $-SO_2N(C_1-C_4alkyl)-$, $-N(C_1-C_4alkyl)SO_2-$, $-CON(C_1-C_4alkyl)-$, $-N(C_1-C_4alkyl)CO-$, $-CH=CH-$, $-CO-$, $-OC(O)-$, $-C(O)O-$ or $N(C_1-C_4alkyl)$ and $(CH_2)_m$ is attached to the naphthyl moiety;

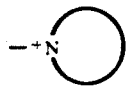

is a 5- or 6-membered monocyclic heterocycle or an 8-, 9- or 10-membered bicyclic heterocycle, the heterocycle containing a first nitrogen in an aromatic 5- or 6-membered first ring, with attachment of the heterocycle to A by way of said first nitrogen and said first nitrogen is quaternary by virtue of the attachment in addition to the ring bonds thereto, with the first ring containing 0 or 1 of either O or S, with the first ring containing 0 to 3 additional nitrogen atoms, with the first ring optionally fused to a 3- or 4-membered moiety to form the optional second ring, with the moiety containing at least one carbon atom, with the moiety containing 0 to 1 of either O or S, with the moiety containing 0 to 2 nitrogen atoms, and with the moiety being saturated or unsaturated and the second ring aromatic or non-aromatic;

$R^c$ is $R^a$ as defined under II below, hydrogen, or —N-$R^yR^z$ (where $R^y$ and $R^z$ are defined in II below), but independently selected from $R^a$ and from each other if more than one $R^c$ is present, and is attached to a carbon ring atom or a nitrogen heteroatom the valency of which is not satisfied by the ring bonds;

I. b)

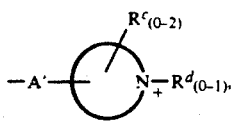

where

is a 5- or 6-membered monocyclic heterocycle or an 8-, 9- or 10-membered bicyclic heterocycle, the heterocycle containing a first nitrogen in an aromatic 5- or 6-membered first ring, with said first nitrogen quaternary by virtue of a substituent $R^d$ in addition to the ring bonds thereto, with said first nitrogen neutral in the absence of a substituent $R^d$, with attachment of the heterocycle to A' by way of a carbon atom of a ring, with the first ring containing 0 or 1 of either O or S, with the first ring containing 0 to 2 additional nitrogen atoms, with the first ring optionally fused to a 3- or 4-membered moiety to form the optional second ring, with the moiety containing at least one carbon atom, with the moiety containing 0 to 1 of either O or S, with the moiety containing 0 to 2 nitrogen atoms, and with the moiety being saturated or unsaturated and the second ring aromatic or non-aromatic;

$R^c$ is as defined above;

$R^d$ is hydrogen, $NH_2$, $O^-$ or $C_1$-$C_4$alkyl (where the alkyl group is optionally mono-substituted with $R^q$ as defined under IIc below);

A' is $(CH_2)_m$—Q—$(CH_2)_n$, where m is 0 to 6 and n is 0 to 6, Q is as given above except that when m and n are both 0 then Q is not a covalent bond and $(CH_2)_m$ is attached to the naphthyl moiety;

I. c) —$A_p$—$N^+R^y(R^w)_{0-1}(R^z)$ where $R^y$ and $R^z$ are as defined under II below, $R^y$ and $R^z$ may further be together a $C_2$-$C_4$ alkylidene radical to form a ring (optionally mono-substituted with $R^q$ as defined below) interrupted by $N(O)R^e$ or $N^+(R^e)_2$ (where $R^e$ is hydrogen, $C_{1-4}$ alkyl, or $C_{1-4}$ alkyl mono-substituted with $R^q$ as defined below), $R^w$ is hydrogen, $C_{1-4}$ alkyl, $O^-$, $NH_2$ or absent in which case the nitrogen is neutral, $R^w$, $R^y$ and $R^z$ may further together form a $C_5$-$C_{10}$ tertiary alkylidene radical which with $N^+$ forms a bicyclic ring, where the tertiary alkylidene radical is optionally mono-substituted with $R^q$ as defined below and where the tertiary carbon of the tertiary alkylidene radical is optionally replaced with nitrogen, $N^+R^e$ (where $R^e$ is defined above), or $N^+$—$O^-$, p is 0 or 1, and A is as defined above;

I. d)

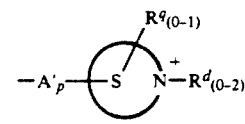

where

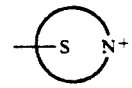

is a 5- or 6-membered monocyclic heterocycle or an 8-, 9- or 10-membered bicyclic heterocycle, the heterocycle containing a first nitrogen in a first ring, with the first ring saturated or unsaturated and non-aromatic, with the first nitrogen quaternary by virtue of one or two substituent $R^d$ in addition to the ring bonds thereto, with the first nitrogen alternatively neutral by virtue of zero or one substituents $R^d$ in addition to the ring bonds thereto, with attachment of the heterocycle to A' by way of a carbon atom or non-quaternary nitrogen atom of a ring, with the first ring containing in addition to carbon and the first nitrogen 0 to 1 of a member selected from the group consisting of the non-quaternary nitrogen of attachment, O, S, S(O), S(O)$_2$ and $NR^e$ where $R^e$ is as defined above, with the first ring optionally fused to a 2-, 3- or 4-membered moiety to form the optional second ring, with the moiety optionally containing in addition to carbon the non-quaternary nitrogen of attachment, and with the moiety saturated or unsaturated and the second ring non-aromatic;

$R^d$ is as defined above and where more than one $R^d$ is present on a nitrogen, at least one $R^d$ is hydrogen or $C_1$-$C_4$alkyl;

A' is as defined above; and p is as defined above;

$R^q$ is as defined below;

and wherein the Type II substituents are:

II.

a) a trifluoromethyl group: —$CF_3$;

b) a halogen atom: —Br, —Cl, —F, or —I;

c) $C_1-C_4$ alkoxy radical: $-OC_{1-4}$ alkyl, wherein the alkyl is optionally mono-substituted by $R^q$, where $R^q$ is a member selected from the group consisting of $-OH$, $-OCH_3$, $-CN$, $-C(O)NH_2$, $-OC(O)NH_2$, $CHO$, $-OC(O)N(CH_3)_2$, $-SO_2NH_2$, $-SO_2N(CH_3)_2$, $-SOCH_3$, $-SO_2CH_3$, $-F$, $-CF_3$, $-COOM^a$ (where $M^a$ is hydrogen, alkali metal, methyl or phenyl), tetrazolyl (where the point of attachment is the carbon atom of the tetrazole ring and one of the nitrogen atoms is mono-substituted by $M^a$ as defined above) and $-SO_3M^b$ (where $M^b$ is hydrogen or an alkali metal);

d) a hydroxy group: $-OH$;

e) a carbonyloxy radical: $-O(C=O)R^s$, where $R^s$ is $C_{1-4}$ alkyl or phenyl, each of which is optionally mono-substituted by $R^q$ as defined above;

f) a carbamoyloxy radical: $-O(C=O)N(R^y)R^z$ where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by $-O-$, $-S-$, $-S(O)-$ or $-S(O)_2-$, to form a ring (where the ring is optionally mono-substituted with $R^q$ as defined above);

g) a sulfur radical: $-S(O)_n-R^s$ where $n=0-2$, and $R^s$ is defined above;

h) a sulfamoyl group: $-SO_2N(R^y)R^z$ where $R^y$ and $R^z$ are as defined above;

i) azido: $N_3$ j) a formamido group: $-N(R^t)(C=O)H$, where $R^t$ is H or $C_{1-4}$ alkyl, and the alkyl thereof is optionally mono-substituted by $R^q$ as defined above;

k) a $(C_1-C_4$ alkyl)carbonylamino radical: $-N(R^t)(C=O)C_{1-4}$ alkyl, where $R^t$ is as defined above, and the alkyl group is also optionally mono-substituted by $R^q$ as defined above;

l) a $(C_1-C_4$ alkoxy) carbonylamino radical: $-N(R^t)(C=O)OC_{1-4}$ alkyl, where $R^t$ is as defined above, and the alkyl group is also optionally mono-substituted by $R^q$ as defined above;

m) a ureido group: $-N(R^t)(C=O)N(R^y)R^z$ where $R^t$, $R^y$ and $R^z$ are as defined above;

n) a sulfonamido group: $-N(R^t)SO_2R^s$, where $R^s$ and $R^t$ are as defined above;

o) a cyano group: $-CN$;

p) a formyl or acetalized formyl radical: $-(C=O)H$ or $-CH(OCH_3)_2$;

q) $(C_1-C_4$ alkyl)carbonyl radical wherein the carbonyl is acetalized: $-C(OCH_3)_2C_{1-4}$ alkyl, where the alkyl is optionally mono-substituted by $R^q$ as defined above;

r) carbonyl radical: $-(C=O)R^s$, where $R^s$ is as defined above;

s) a hydroximinomethyl radical in which the oxygen or carbon atom is optionally substituted by a $C_1-C_4$ alkyl group: $-(C=NOR^z)R^y$ where $R^y$ and $R^z$ are as defined above, except they may not be joined together to form a ring;

t) a $(C_1-C_4$ alkoxy)carbonyl radical: $-(C=O)OC_{1-4}$ alkyl, where the alkyl is optionally mono-substituted by $R^q$ as defined above;

u) a carbamoyl radical: $-(C=O)N(R^y)R^z$ where $R^y$ and $R^z$ are as defined above;

v) an N-hydroxycarbamoyl or $N(C_1-C_4$ alkoxy)carbamoyl radical in which the nitrogen atom may be additionally substituted by a $C_1-C_4$ alkyl group: $-(C=O)-N(OR^y)R^z$ where $R^y$ and $R^z$ are as defined above, except they may not be joined together to form a ring;

w) a thiocarbamoyl group: $-(C=S)N(R^y)R^z$ where $R^y$ and $R^z$ are as defined above;

x) carboxyl: $-COOM^b$, where $M^b$ is as defined above;

y) thiocyanate: $-SCN$;

z) trifluoromethylthio: $-SCF_3$;

aa) tetrazolyl, where the point of attachment is the carbon atom of the tetrazole ring and one of the nitrogen atoms is mono-substituted by hydrogen, and alkali metal or a $C_1-C_4$ alkyl optionally substituted by $R^q$ as defined above;

ab) an anionic function selected from the group consisting of: phosphono $[P=O(OM^b)_2]$; alkylphosphono $\{P=O(OM^b)-[O(C_1-C_4$ alkyl$)]\}$; alkylphosphinyl $[P=O(OM^b)-(C_1-C_4$ alkyl$)]$; phosphoramido $[P=O(OM^b)N(R^y)R^z$ and $P=O(OM^b)NHR^x]$; sulfino $(SO_2M^b)$; sulfo $(SO_3M^b)$; acylsulfonamides selected from the structures $CONM^bSO_2R^x$, $CONM^bSO_2N(R^y)R^z$, $SO_2NM^bCON(R^y)R^z$; and $SO_2NM^bCN$, where $R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by $R^q$, as defined above; $M^b$ is as defined above; and $R^y$ and $R^z$ are as defined above;

ac) $C_5-C_7$ cycloalkyl group in which one of the carbon atoms in the ring is replaced by a heteroatom selected from O, S, NH or $N(C_1-C_4$ alkyl) and in which one additional carbon atom may be replaced by NH or $N(C_1-C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) $C_2-C_4$ alkenyl radical, optionally mono-substituted by one of the substituents a) to ac) above and phenyl which is optionally substituted by $R^q$ as defined above;

ae) $C_2-C_4$ alkynyl radical, optionally mono-substituted by one of the substituents a) to ac) above;

af) $C_1-C_4$ alkyl radical;

ag) $C_1-C_4$ alkyl mono-substituted by one of the substituents a)-ac) above;

ah) a 2-oxazolidinonyl moiety in which the point of attachment is the nitrogen atom of the oxazolidinone ring, the ring oxygen atom is optionally replaced by a heteroatom selected from $-S-$ and $>NR^t$ (where $R^t$ is as defined above) and one of the saturated carbon atoms of the oxazolidinone ring is optionally mono-substituted by one of the substituents a) to ag) above;

M is selected from:

i) hydrogen;

ii) a pharmaceutically acceptable esterifying group of removable carboxyl protecting group;

iii) an alkali metal or other pharmaceutically acceptable cation; and iv) a negative charge which is balanced by a positively charged group.

Also provided are novel intermediates for carbapenem compounds of the formula:

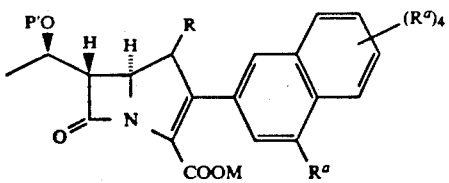

wherein:
R is H or CH₃;
$R^a$ is defined above, with the proviso that $R^q$ additionally includes OP' where P' is defined below, that $M^a$ and $M^b$ of $R^q$ both include M and that $R^a$ additionally may be protected hydroxyl, OP';
P' is a removable protecting group for hydroxy;
M is a removable carboxyl protecting group; and the Type I, $R^a$ substituent is balanced with the anionic form of Z where
Z is methanesulfonyloxy, trifluoromethanesulfonyloxy, fluorosulfonyloxy, p-toluenesulfonyloxy, 2,4,6-triisopropylbenzenesulfonyloxy, p-bromobenzenesulfonyloxy, p-nitrobenzenesulfonyloxy, bromo and iodo.

Additional preferred intermediates have the formula:

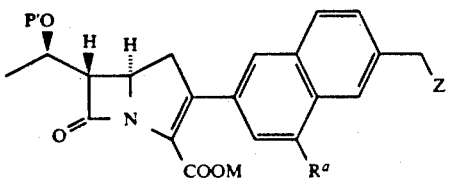

wherein
$R^a$ is selected from the group consisting of H, Cl, Br, I, SCH₃, CN, CHO, SOCH₃, SO₂CH₃, CO₂M, CONH₂, OP' and CH₂OP';
P' is a removable protecting group for hydroxy;
M is a removable protecting group for carboxyl; and
Z is selected from the group consisting of alkylsulfonyloxy, substituted alkylsulfonyloxy arylsulfonyloxy, substituted arylsulfonyloxy, fluorosulfonyloxy and halogen.

DETAILED DESCRIPTION OF THE INVENTION

The manufacture of compounds of Formula I may be carried out in a three-stage synthesis scheme followed by removal of protecting groups. The objective of the first synthesis stage is to produce a base bromonaphthalene compound which may be converted to the two-position substituent of the carbapenem of Formula I. The objective of the second synthesis stage is to attach the base naphthalene to the carbapenem. Finally, the objective of the third synthesis stage is to substitute the naphthalene with the desired $R^a$. This third synthesis stage may be performed after the first synthesis stage or during or after the second synthesis stage according to the nature of the various $R^a$.

Flow Sheet A demonstrates a suggested first stage synthesis. Flow Sheets B and C demonstrate two alternative second stage synthesis. The third synthesis varies according to the selected $R^a$.

The first synthesis stage, the synthesis of a substituted bromonaphthalene compound, can be achieved by many processes well-known in the art. The synthesis, substitution, and elaboration of naphthalenes, including bromonaphthalenes, has been thoroughly reviewed in the chemical literature; E. H. Rodd and J. van Alphen in Rodd's Chemistry of Carbon Compounds, Vol. III, Part B, Aromatic Compounds, p. 1253 (1956); N. Campbell in Rodd's Chemistry of Carbon Compounds, 2nd Edition, Vol. III, Part G, Aromatic Compounds, p. 99 (1978); M. J. S. Dewar and P. J. Grisdale, J. Am. Chem. Soc., 84, 3541 (1962); W. Adcock and P. R. Wells, Aust. J. Chem., 18, 1351 (1965); W. Adcock and M. J. S. Dewar, J. Am. Chem Soc., 89, 386 (1967); W. Adcock et al., J. Am. Chem. Soc., 97, 2198 (1975); E. A. Dixon et al, Can. J. Chem., 59 2629 (1981). Flow Sheet A below shows a representative starting bromonaphthalene compound, A1.

Employing naphthalene A1, a starting material B1 for the suggested second stage synthesis may be produced. Referring to Flow Sheet A, and starting with A1, it is first necessary to convert the 1-position carboxyl to a desired $R^a$ substituent, or precursor substituent thereto which is stable to the reaction conditions of adding the naphthalene to a substituted azetidin-2-one precursor of the desired carbapenem. A t-butyldimethylsilyloxymethyl precursor substituent may be obtained on the 1-position of A1 in two steps. Firstly, the carboxyl is reduced to hydroxymethyl by reacting A1 with a reducing agent, such as lithium aluminum hydride (LAH), borane, or the like, in a suitable polar aprotic solvent, such as THF, diethyl ether, or the like, at 0° C. to room temperature (RT). Secondly, the reaction product is isolated and reacted with t-butyldimethylsilyl chloride in dichloromethane with triethylamine and 4-dimethylaminopyridine to produce protected naphthalene B1.

As to the $R^a$ substituent on compound A1, it may be an $R^a$ with or without protecting groups stable to the conditions of producing compound B1 and stable to the conditions of subsequently adding B1 to the carbapenem. Alternatively, it may be a stable precursor substitutent which is stable to the conditions of making B1, which is optionally stable to the conditions of adding B1 to the carbapenem and which is convertible to a desired $R^a$ or to another precursor substituent. The identity of the precursor substituent employed is not crucial so long as it does not interfere with synthesis to B1 and so long as it may be thereafter converted to more desirable substitution. Preferred precursor substituents are methyl, hydroxymethyl and protected hydroxymethyl.

With stable $R^a$ or suitable precursor substituents thereof, naphthalene B1 may be added to azetidin-2-one B2 in a Grignard reaction as shown in Flow Sheet B. The Grignard reaction requires that B1 be converted to a Grignard reagent by reaction with magnesium and 1,2-dibromoethane in a suitable polar aprotic solvent, such as THF, diethyl ether, or the like, from 20° C. to 60° C. and subsequently contacting B1 as a Grignard reagent with B2 in a suitable polar aprotic solvent, such as THF, diethyl ether, or the like, at from −70° C. to about 20° C. to produce azetidin-2-one B3. Alternatively, B1 may be reacted with t-butyllithium, n-butyllithium, or the like in a suitable polar aprotic solvent, such as THF, diethyl ether, or the like, at from −78° to −50°

C. followed by the addition of magnesium bromide to produce the same Grignard reagent. $R^i$ of B3 is in practice pyrid-2-yl but may clearly be a variety of substituents including aromatic and heteroaromatic substituents. Further $R^i$ might be form example phenyl, pyrimidinyl or thiazolyl.

Azetidin-2-one B3 is an intermediate that may be ring closed to a carbapenem. It is on this intermediate that $R^a$ or precursor substituent such as t-butyldimethylsilyloxymethyl should be modified where such modification is incompatible with the carbapenem nucleus. For example, a convenient reaction to remove the t-butylidimethylsilyl group from the 1-position hydroxymethyl substituent of the naphthalene on compound B3 is to expose compound B3 to a diluted solution of sulfuric acid in methanol at 0° C. Flow Sheet B shows the resulting compound B3A. If the t-butyldimethylsilyl group was removed under the same conditions after cyclization of B3 to a carbapenem, a substantial portion of carbapenem would be degraded and lost. Thus, modification of the precursor substituent in this instance and replacement with another precursor substituent or even $R^a$ is best performed before closing the carbapenem. Of course it is possible to remove the t-butylimethylsilyl group in reduced yield after cyclization of B3 to a carbapenem by reaction with tetra-n-butylammonium fluoride and acetic acid in THF.

Compound B3A may be ring closed to carbapenem B4 by refluxing in xylene with a trace of p-hydroquinone for about 1 to 2 hours. It is on this intermediate that final elaboration of $R^a$ from a precursor substituent, e.g. hydroxymethyl, may be accomplished. Removal of the protecting groups then provides the final compound Formula I. Such final elaboration and deprotection is described in further detail below.

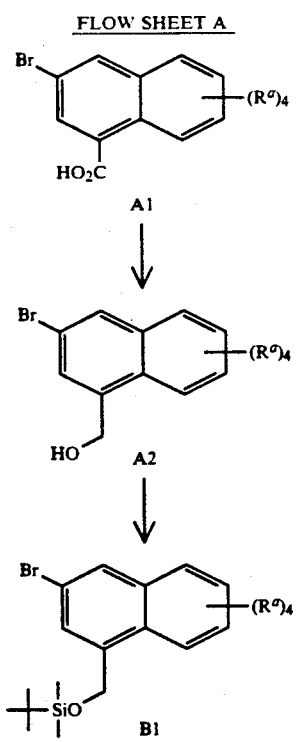

FLOW SHEET A

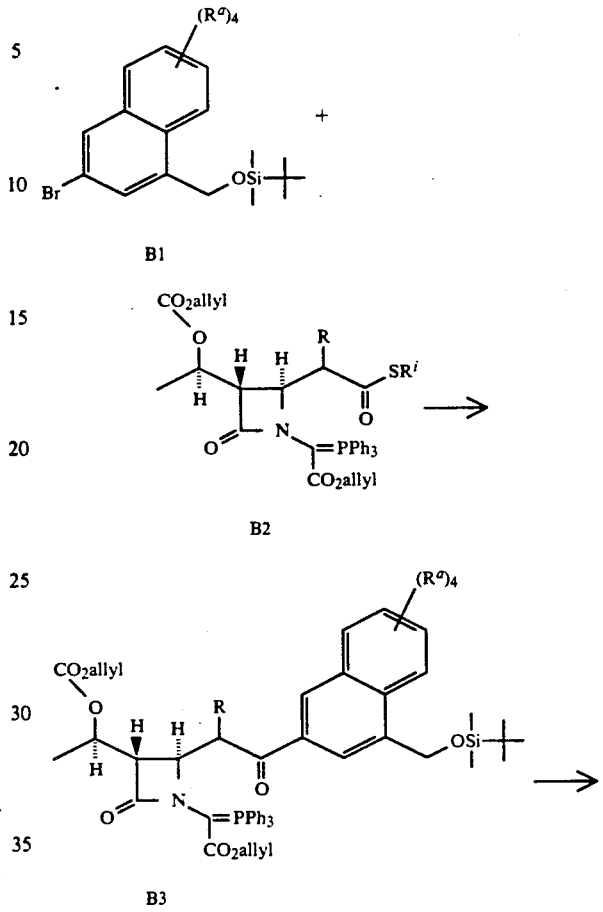

FLOW SHEET B

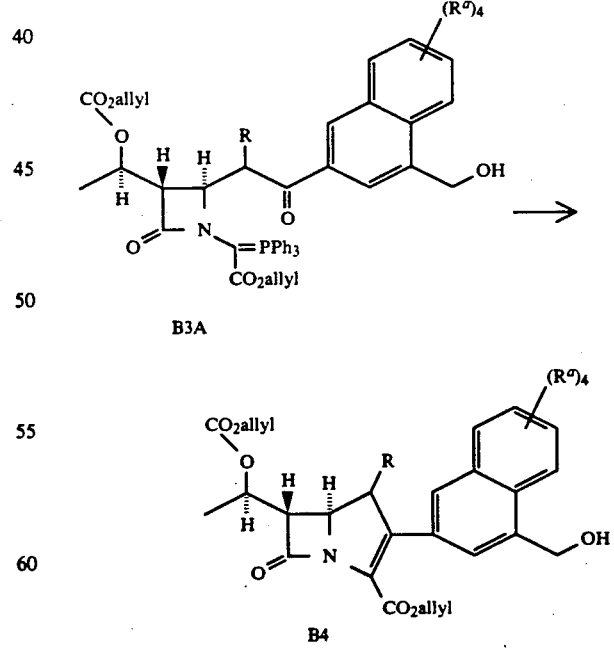

Flow Sheet C shows an alternative second stage synthesis, i.e. attachment of the base naphthalene such as B1 to the 2-position of the carbapenem. This synthesis involves a palladium catalyzed cross-coupling reaction between a carbapenem triflate and a suitably substituted arylstannane, a process which is described in U.S. patent application Ser. No. 485,096 filed Feb. 26, 1990, hereby incorporated by reference. In order to apply this synthesis, it is first necessary to modify bromonaphthalene B1 to the trimethylstannylnaphthalene C3. This is accomplished by reacting B1 with t-butyllithium in THF at from −78° to −50° C. followed by the addition of trimethyltin chloride. This provides an intermediate from which the t-butyldimethylsilyl protecting group on the 1-position hydroxymethyl substituent is removed by exposure to tetra-n-butylammonium fluoride in THF yielding C3. Alternatively, bromonaphthalene B1 may be reacted with hexamethylditin in the presence of a palladium(O) catalyst such as tetrakis(triphenylphosphine)palladium in an inert solvent such as toluene at from 25° to 110° C. for from 0.25 to 24 hours to provide, after removal of the t-butyldimethylsilyl protecting group as described above, the same stannane C3. If the t-butyldimethylsilyl group was removed under the same conditions after attachment of the naphthalene side chain to the carbapenem, a much reduced overall yield would be obtained due to degradation of the carbapenem during such a removal. Thus modification of the precursor substituent in this instance and replacement with another precursor substituent or even $R^a$ is best performed before attachment to the carbapenem. Referring to Flow Sheet C, the 2-oxocarbapenam C1 is reacted with a suitable trifluoromethanesulfonyl source, such as trifluoromethanesulfonic anhydride, trifluoromethanesulfonyl chloride and the like, in the presence of an organic nitrogen base, such as triethylamine, diisopropylamine and the like, in polar aprotic solvent, such as tetrahydrofuran. An organic nitrogen base, such as triethylamine and the like, is then added to the reaction solution followed immediately by a silylating agent, such as trimethylsilyl trifluoromethanesulfonate to provide intermediate C2. An aprotic polar coordinating solvent, such as DMF, 1-methyl-2-pyrrolidinone and the like, is added. This is followed by the addition of a palladium compound, such as tris(dibenzylideneacetone)dipalladium-chloroform, palladium acetate, bis(acetonitrile)palladium(II).chloride and the like, and the stannane C3. Addition of a suitably substituted arylphosphine, such as tris(4-methoxyphenyl)phosphine, tris(2,4,6-trimethoxyphenyl)phosphine, trifurylphosphine and the like, may also be beneficial. A metal halide, such as lithium chloride, zinc chloride and the like, is added and the reaction solution is warmed to a suitable temperature, such as 0° to 50° C., and allowed to stir for a suitable amount of time, such as from a few minutes to 48 hours. The carbapenem C4 is obtained by conventional isolation/purification methodology known in the art.

Generally speaking, the milder conditions of the synthesis shown in Flow Sheet C allow for a wider range of functional groups $R^a$ to be present when attaching the naphthalene, than the synthesis illustrated in Flow Sheet B. However, in certain cases it is advantageous for the $R^a$ substituent(s) of the stannane C3 to be introduced in a protected or precursory form. Final elaboration of $R^a$ from a precursor substituent, e.g. hydroxymethyl, may be accomplished on carbapenem intermediate C4. Removal of protecting groups then provides the final compound of Formula I. Such final elaboration and deprotection is described in further detail below.

FLOW SHEET C

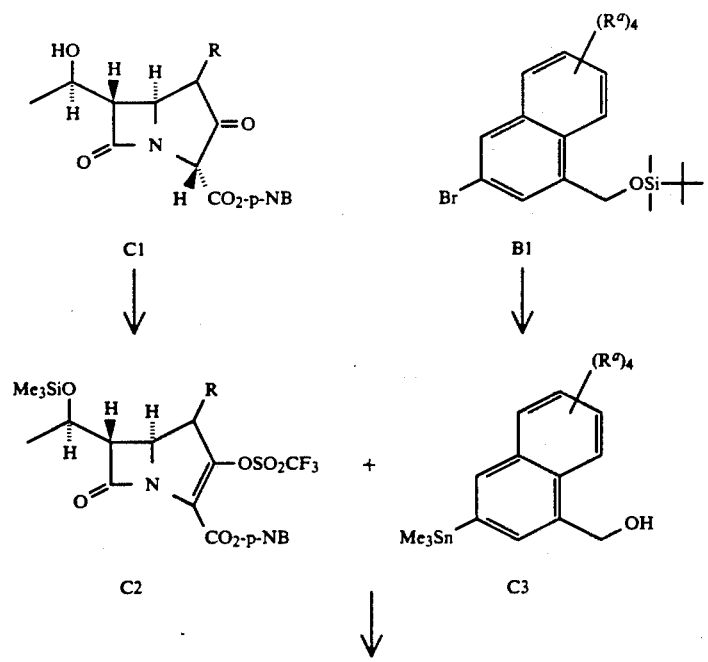

FLOW SHEET C

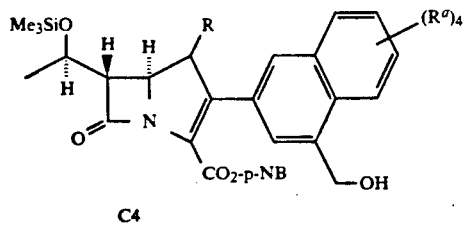

C4 p-NB = 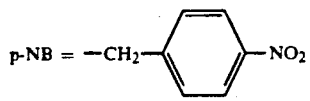

Azetidin-2-one B2, a pyridyl-thioester, is a well known compound in the production of carbapenems. Diverse synthetic schemes useful to make B2 may be imagined by the skilled artisan. Particularly useful to the instant invention is a synthetic scheme set out further in Flow Sheet D below in which the symbol R is as defined above. The steps for preparing intermediate B2 are analogous to the procedures described, for example, in U.S. Pat. Nos. 4,260,627 and 4,543,257; L. D. Cama et al. *Tetrahedron*, 39, 2531 (1983); R. N. Guthikonda et al. *J. Med. Chem.*, 30, 871 (1987).

FLOW SHEET D

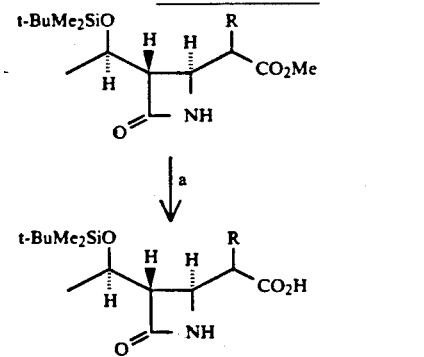

↓ a

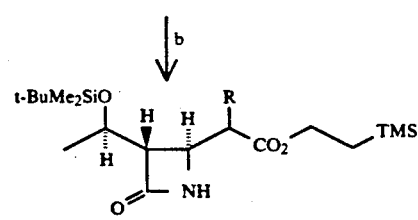

↓ b

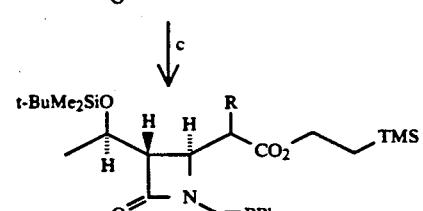

↓ c

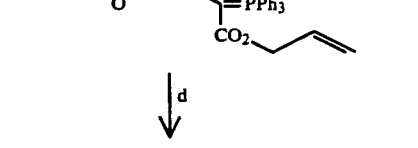

↓ d

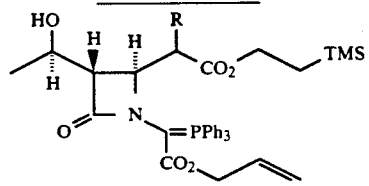

↓ e

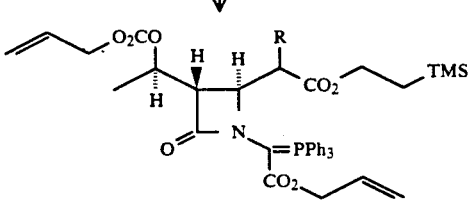

↓ f

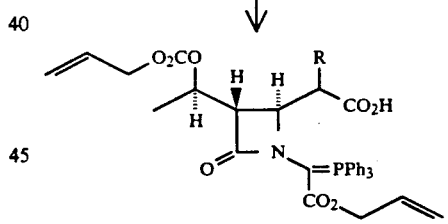

↓ g

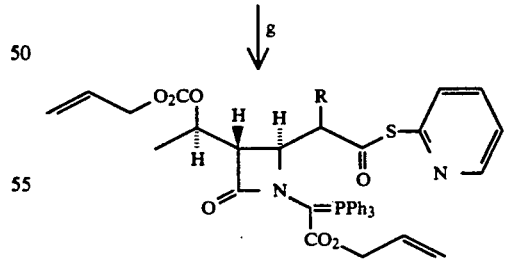

B2 a. NaOH/MeOH
b. carbonyl diimidazole/ HOCH₂CH₂TMS
c. i. OHCCO₂CH₂CH=CH₂
   ii. SOCl₂
   iii. Ph₃P
d. 6N HCl/MeOH
e. ClCO₂CH₂CH=CH₂/DMAP

-continued
FLOW SHEET D f. nBu₄NF
g. Pyr-SS-Pyr./Ph₃P

The steps for preparing the 2-oxocarbapenam intermediate Cl are well known in the art and are explained in ample detail by D. G. Melillo et al., *Tetrahedron Letters*, 21, 2783 (1980), T. Salzmann et al., *J. Am. Chem. Soc.*, 102, 6161 (1980), and L. M. Fuentes, I. Shinkai, and T. N. Salzmann, *J. Am. Chem. Soc.*, 108, 4675 (1986). The syntheses are also disclosed in U.S. Pat. No. 4,269,772, U.S. Pat. No. 4,350,631, U.S. Pat. No. 4,383,946 and U.S. Pat. No. 4,414,155 all assigned to Merck and Company, Inc.

The general synthesis description depicted above in the Flow Sheets shows a protected 1-hydroxyethyl substitution on the 6-position of the carbapenem. After final deprotection, a 1-hydroxyethyl substituent is obtained, which is preferred in most cases. However, it has been found that with certain 2-side-chain selections, the ultimate balance of favorable properties in the overall molecule may be enhanced by selection of the 6-(1-fluoroethyl) moiety instead. Preparation of 6-fluoroalkyl compounds within the scope of the present invention is carried out in a straightforward manner using techniques well known in the art of preparing carbapenem antibacterial compounds. See, e.g., J. G. deVries et al., *Heterocycles*, 23 (8), 1915 (1985); BE 900 718 A (Sandoz) and Japanese Patent Pub. No. 6-0163-882-A (Sanraku Ocean).

In the compounds of the present invention, one of the $R^a$ substituents must be of Type I. As a general matter, it is conjectured that anti-MSRA/MRCNS activity results from the configuration of the overall molecule uniquely conferred by the naphthalene nucleus. The Type I substituent provides still greater anti-MRSA/MRCNS activity to the molecule.

The Type II substituents are distinguishable from Type I substituents chemically and with respect to the biological properties which they confer. In related compounds, it has been found that the Type II substituted compounds afford greater water solubility and reduced potential for CNS side effects. Substituents which tend to confer improved water solubility on the overall compound have been found useful, since they are contemplated to thereby improve the transport of the compound involved. Although a substantial number and range of Type II substituents have been described herein, all of these are contemplated to be a part of the present invention based on the biological performance of substituents related in terms of their medicinal chemistry.

Since it is possible to combine, in the compounds of the present invention, the required Type I substituent with the optional Type II substituents, there can be obtained a combination of desired attributes in the final overall molecule not attainable with a single substituent, i.e., improved anti-MRSA/MRCNS activity together with enhanced water solubility.

All of the Type I substituents employed in the compounds of the present invention may have quaternary nitrogen groups, and these include both cyclic and acyclic types, as is described under Type I hereinabove. As already pointed out above, it is required that one, but no more than one, of the substituents $R^a$ must be a member selected from the group consisting of the definitions under Type I. It is optional that one, or at most three, of the remaining substituents may be a member selected from the group consisting of definitions under Type II. For example, $R^a$ at position 7- may be a Type I substituent and $R^a$ at position 1- may be of Type II, while the remaining substituents are hydrogen.

In preferred compounds of Formula I, $R^1$ is hydrogen. More preferably, $R^1$ is hydrogen and $R^2$ is (R)—CH₃CH(OH)— or (R)—CH₃CH(F)—. In the most preferred case, $R^1$ is hydrogen and $R^2$ is (R)—CH₃CH(OH)—. While R=H is usually preferred, there are instances in which R=CH₃ may provide improved chemical stability, water solubility, or pharmacokinetic behavior. The substituent R=CH₃ may be of either configuration, i.e., the α or β-stereoisomer. Additionally, in preferred compounds, at least one $R^a$ in the 1- or 7- position of the naphthalene is other than hydrogen.

Preferred Type I. a) substituents include:

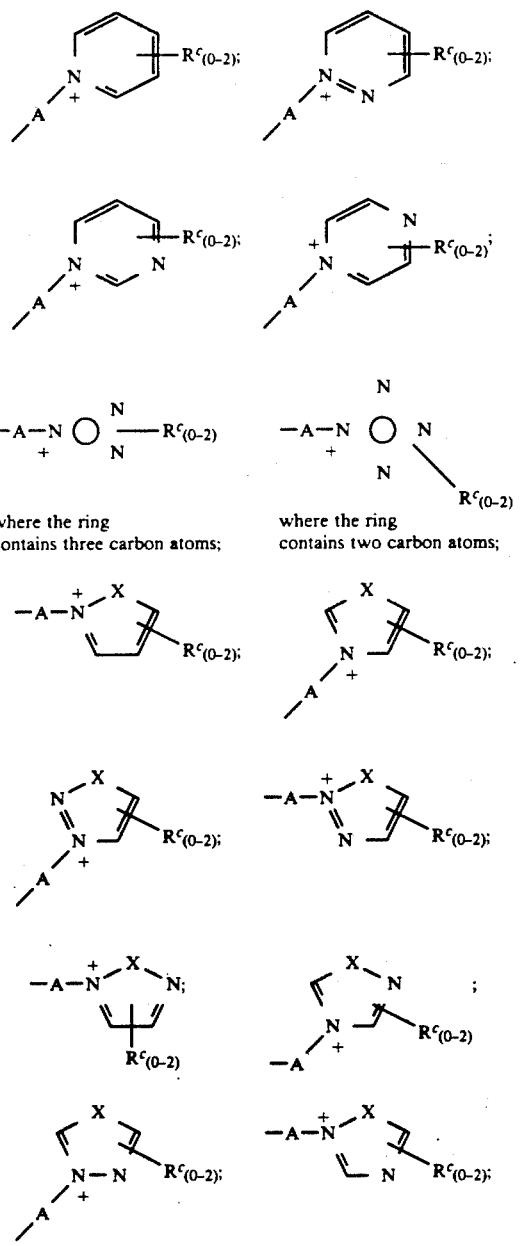

-continued where X=O, S, or NR$^c$. For structures of Type I. a), where R$^c$ is shown to have an indefinite position, it may be attached to any carbon of the ring.

Preferred Type I. b) substituents include:

where the ring contains three carbon atoms

-continued

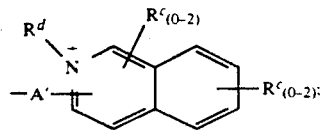

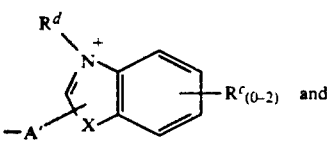

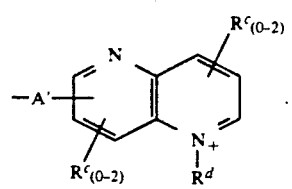

where X=O, S, or NR$^c$ and X'=O or S. For structures of Type I. b), where R$^c$ and/or A' are shown to have indefinite positions, they are independently attached to any carbon atom of the ring.

Preferred Type I. c) substituents include:

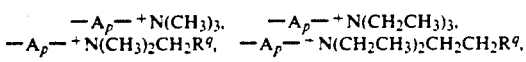

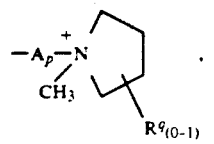 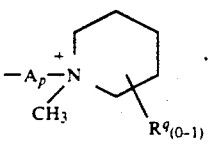

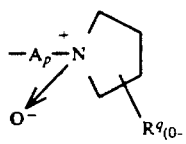 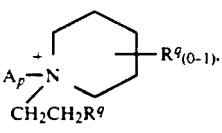

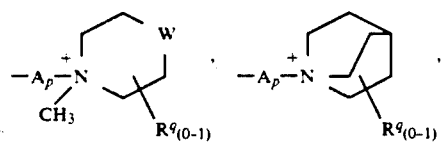

where W is O, S, NR$^e$, N(O)R$^e$, SO, SO$_2$ or N+(R$^e$)$_2$ and W' is N+R$^e$ or NO. For structures of Type I. c), where R$^q$ is shown to have an indefinite position, it may be attached to any carbon atom of the ring.

Preferred Type I. d) substituents include:

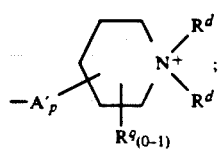

-continued

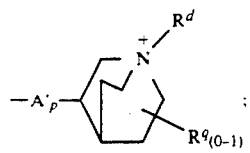

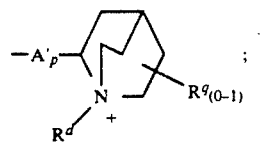

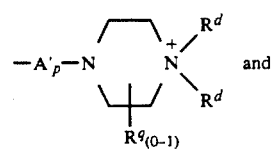 and

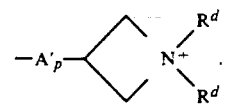

For structures of Type I. d), where R$^q$ and/or A'$_p$ is shown to have an indefinite position, it may be attached to any carbon atom of the ring.

The R$^c$ substituents herein are intended to represent suitable further substituents on the Type I. a) or b) substituents for the naphthyl ring. As seen above, these Type I. a) or b) substituents are monocyclic or bicyclic aromatic groups containing heteroatoms. Given this class of primary substituent, further suitable substituents may be readily discovered in the carbapenem art. For example, suitable substituents for Type I. a) or b) substituents are generally taught in U.S. Pat. No. 4,729,993 assigned to Merck and Co. or in U.S. Pat. No. 4,746,736 assigned to Bristol-Myers Co. These patents are hereby incorporated by reference.

Broadly, R$^c$ may be the same or different and may be selected on an independent basis from the group as defined above. While a single such substitution is preferred, there is occasssion to use up to two such substituents on an R$^a$, e.g., where it is desired to enhance the effect of a particular substituent group by employing multiple substituents. The particular choice of R$^c$ will depend upon the situation. For instance, a specific R$^c$ may lend particular stability to a nitrogen cation. At other times it may be desired to employ a substituent known to enhance antibacterial activity of the overall molecule against a particular bacterium, for example, while also employing a substituent known to improve some other property such as water solubility or the duration of action of the overall molecule.

The scope of R$^c$ herein includes two specific types of further substituent attached to the Type I. a) or b) substituent. A first type of R$^c$ are those attached to a ring carbon and a second type of R$^c$ are those attached to a neutral ring nitrogen. Persons skilled in the art will readily recognize that a wide range of organic substituents are suitably used as R$^c$. Persons skilled in the art will also recognize that some substituents including the —NR$^y$R$^z$ substituents, useful for one purpose of R$^c$, i.e. carbon substitution, are not equally useful in the other, i.e. nitrogen substitution.

Preferred $R^c$ attached to ring carbon atoms are —NH$_2$, —SCH$_3$, —SOCH$_3$, —CH$_2$OH, —(CH$_2$)$_2$OH, —OCH$_3$, —COOM$^b$, —CH$_2$COOM$^b$, —CH$_2$CH$_2$COOM$^b$, —CH$_2$SOCH$_3$, —CH$_2$SCH$_3$, —SO$_3$M$^b$, —CH$_2$SO$_3$M$^b$, —CH$_2$CH$_2$SO$_3$M$^b$, —Br, —Cl, —F, —I, —CH$_3$, CH$_2$CH$_3$, CH$_2$CONH$_2$ and CH$_2$CON(C$_1$-C$_4$alkyl) where $M^b$ is defined above. Preferred $R^c$ attached to neutral ring nitrogen atoms are —CH$_2$OH, —(CH$_2$)$_2$OH, —CH$_2$COOM$^b$, —CH$_2$CH$_2$COOM$^b$, —CH$_2$SOCH$_3$, —CH$_2$SCH$_3$, —CH$_2$SO$_3$M$^b$, —CH$_2$CH$_2$SO$_3$M$^b$, —CH$_3$, CH$_2$CH$_3$, CH$_2$CONH$_2$ and CH$_2$CON(C$_1$-C$_4$alkyl) where $M^b$ is defined above.

It is preferred that each Type I. a) or b) substituent have no more than two $R^c$ substituents which are other than hydrogen. Thus, the formula shown above for Type I. a) substituents has up to two $R^c$ substituents with the remainder of course being hydrogen. Further, the formula for the Type I. b) substituent also allows up to two $R^c$. In accordance with these formulae, the previously listed more specific structures should be interpreted to have no more than two $R^c$ for each monocyclic or bicyclic group. Similarly for Type I. c) or d) substituents it is preferred that any monocylic or bicyclic group have no more than a single $R^q$ substituent.

The scope of $R^d$ includes a single Type of further substituent attached a Type I. b) or d) substituent. The $R^d$ substituents are attached to a cationic nitrogen which may or may not be aromatic. Preferred $R^d$ attached to cationic nitrogen atoms are hydrogen, —CH$_3$, CH$_2$CH$_3$, —CH$_2$CH$_2$CH$_3$, —CH$_2$COOM$^b$, —CH$_2$SO$_3$M$^b$, —NH$_2$ and O$^{(-)}$, where $M^b$ is defined above.

The formulas depicting Type Ib, Ic, and Id substituents show positively charged states for those substituents. It is understood that certain of those substituents, which are cationic by virtue of having a protonating hydrogen atom attached to the nitrogen, may also exist or be produced under certain conditions as a neutral substituent by virtue of the absence of such a hydrogen atom (i.e. in Type Ib, when there is no $R^d$; in Type Ic, when there is no $R^w$; and in Type Id, when there is zero to one $R^d$, depending on type of heterocycle). Whether such a Type Ib, Ic, or Id substituent will be predominately cationic or neutral in a given physical state will be governed by principles of acid-base chemistry, which are well known to those skilled in the art. For example, the particular ratio of neutral form to cationic form will depend upon the basicity of the amine and acidity of a solution. When such a substituent is in a protonated quaternized state, the compound exists as a zwitterion which is internally balanced as to charge or as an ammonium salt which is externally balanced. In illustration, if there is no $R^d$ on a Type Ib substituent, it is understood that such a substituent is neutral (there is no positive charge on the nitrogen). A compound containing such a substituent is typically produced in this form as a salt, wherein M is an alkali metal, and may exist in solution in its neutral form. However, depending upon conditions, a compound containing a neutral Type Ib substituent may be in equilibrium with, and may also be represented by a formula showing, the corresponding compound containing the quaternized protonated substituent where $R^d$ is present and is a hydrogen atom. Furthermore the same compound may exist with the Type Ib substituent in a completely protonated quaternized form, for instance in an aqueous solution in the presence of a stoichiometric amount of a strong mineral acid. It is intended herein that both the protonated (cationic) and the unprotonated (neutral) forms of Types Ib, Ic and Id substituents of the kinds just described are within the scope of the present invention.

Suitable A spacer moieties include —CH$_2$—, —CH$_2$CH$_2$—, —CH$_2$CH$_2$CH$_2$—, —CH$_2$CH$_2$CH$_2$CH$_2$—, —OCH$_2$CH$_2$—, —SOCH$_2$—, —SO$_2$CH$_2$—, —SCH$_2$CH$_2$—, —SOCH$_2$CH$_2$—, —SO$_2$CH$_2$CH$_2$—, —NHCH$_2$CH$_2$—, —N(CH$_3$)CH$_2$CH$_2$—, —CH$_2$N(CH$_3$)CH$_2$CH$_2$—, —CONHCH$_2$CH$_2$—, —SO$_2$NHCH$_2$CH$_2$—, —COCH$_2$—, —CH=CHCH$_2$— and —CH$_2$OCH$_2$CH$_2$—. Preferably, where Q is O, S, NH or N(C$_{1-4}$alkyl), then n is 2-6.

Suitable A' are listed for A above. Further A' may suitably be —O—, —S—, —NH—, —SO$_2$—, —SO$_2$NH—, —CONH—, —CH=CH—, —CH$_2$S—, —CH$_2$NH—, —CONHCH$_2$— or —SO$_2$NHCH$_2$—.

It is understood that the chemical formulas defining A and A' spacers are to be read in a normal left to right manner and are not to be read in any other direction. Thus (CH$_2$)$_m$—Q—(CH$_2$)$_n$ is not equivalent to, and should not be read as, (CH$_2$)$_n$—Q—(CH$_2$)$_m$.

The Type I. cationic substituents are generally added to the naphthalene following attachment of the naphthalene to the carbapenem. Conveniently, the naphthalene side-chain should be synthesized with a precusor substituent which may be elaborated into the desired cationic substituent. The identity of the precursor substituent will vary according to the particular $R^q$ desired. For example, one such precursor substituent is —A—OH, such as hydroxymethyl.

The hydroxymethyl precursor substituent may be elaborated into cationic substituents of Type I.a) by converting the hydroxyl into an active leaving group such as an iodide (giving —A—I) followed by reaction with a desired nitrogen containing aromatic compound. More particularly, two alternative procedures may be utilized to produce a leaving group on the moiety —A— and subsequently to replace such a leaving group with cationic substituents of the type just described.

For a first procedure, the hydroxyl group of —A—OH may be converted to a methanesulfonate group by treating with methanesulfonyl chloride in the presence of triethylamine. A suitable solvent, e.g., dichloromethane, is employed and the reaction is carried out at reduced temperatures. In turn, the methanesulfonate intermediate which itself is a good leaving group may be converted to the reactive iodide derivative by treatment with sodium iodide in a suitable solvent, e.g., acetone, at reduced or ambient temperatures. Alternatively, the hydroxyl group may be directly converted into the iodide group by common methods known to the art. For example, treatment of the hydroxyl group with methyl triphenoxyphosphonium iodide in a suitable solvent, such as dimethylformamide, at reduced or ambient temperatures, directly provides the desired iodide. Once the iodide has been formed, the introduction of the cationic substituent is accomplished simply by treating the iodide with the desired nitrogen containing compound, e.g. a heteroaromatic compound such as pyridine. The reaction will proceed in a suitable solvent, such as acetonitrile, at or about room temperature. This displacement reaction may also be facilitated by the addition of excess silver trifluoromethanesulfonate to the reaction mixture, in which case reduced temperatures are often desireable.

For a second procedure, the hydroxyl group of —A—OH may be converted into the reactive trifluoromethanesulfonate (triflate) group. However, such an activating group cannot be isolated by conventional techniques but may be formed and used in situ. Thus, treatment of the hydroxyl group with trifluoromethanesulfonic (trific) anhydride in the presence of a hindered, non-nucleophilic base such as 2,6-lutidine, 2,4,6-collidine, or 2,6-di-tert-butyl-4-methylpyridine in a suitable solvent, such as dichloromethane, at reduced temperatures provides for the generation of the triflate activating group. Introduction of the cationic group is then accomplished by reacting the above triflate in situ with the desired nitrogen containing compound at reduced temperature. In certain cases it is possible and desirable to use the reacting nitrogen containing compound as the base for the formation of the triflate activating group. In this case treatment of the hydroxyl group with triflic anhydride in the presence of at least two equivalents of the reacting nitrogen compound under the conditions described above provides the cationic substituent.

The above are representative of suitable leaving groups: alkylsulfonyloxy, substituted alkylsulfonyloxy, arylsulfonyloxy, substituted arylsulfonyloxy, fluorosulfonyloxy and halogen. The common sulfonate leaving groups are: methanesulfonyloxy, trifluoromethanesulfonyloxy, fluorosulfonyloxy, p-toluenesulfonyloxy, 2,4,6-tri-isopropylbenzenesulfonyloxy, p-bromobenzenesulfonyloxy and p-nitrobenzenesulfonyloxy. The preferred halo leaving groups are bromo and iodo. These alkyl and arylsulfonate leaving groups may be prepared using an analogous route to the one described above using the sulfonyl chloride or the sulfonic anhydride.

Where the cationic substitution has a substituent $R^c$, the most facile method of providing such a substituent is to employ as the reactant in the preparation methods described above a nitrogen containing compound which already has the desired substituent. Such substituted compounds are readily available starting materials or may be prepared in a straight-forward manner using known literature methods.

The Type I.b) cationic substituents are prepared by quaternization of an aromatic ring nitrogen of a neutral precursor substituent on the naphthalene ring. Examples of neutral precursor substituents are —CONHCH$_2$—(2-pyridyl), —CONHCH$_2$—(4-pyridyl) or —SO$_2$CH$_2$—(4-pyridyl). Quaternization is accomplished by reacting the nitrogen compound in an inert organic solvent (e.g. CH$_2$Cl$_2$) at about 0° C. to room temperature with an alkylating agent $R^d$—Y where $R^d$ is given above and Y is a leaving group such as iodide, bromide, mesylate (methanesulfonate), tosylate (p-toluenesulfonate) or triflate. Alternatively, the aromatic ring nitrogen may be quaternized by reaction with an oxidizing agent such as 3-chloroperbenzoic acid (giving the N-oxide) or an amidinating reagent such as o-(2,4,6-triisopropylbenzenesulfonyl)hydroxylamine (giving the N-amino derivative) in a suitable solvent (e.g. dichloromethane or CH$_3$CN) at about room temperature. In addition, the neutral precursor substituent may be rendered cationic through protonation of the basic aromatic ring nitrogen. This may be accomplished by treatment of the neutral precursor with a suitable inorganic or organic acid, e.g. hydrochloric acid, phosphoric acid, hydrobromic acid, acetic acid or benzoic acid. Protonation may further be accomplished by a carboxylic acid function elsewhere in the molecule, including the C-3 carboxyl on the carbapenem. The neutral precursor substituent may be already attached to the naphthalene ring at the time of its connection to the carbapenem, or it may be elaborated from a simpler precursor after connection to the carbapenem. An example of a precursor substituent for elaboration is —A′—OH such as hydroxymethyl. In one suggested synthesis, the hydroxyl may be converted to a reactive leaving group such as iodo as described above. The iodide is then reacted in a nucleophilic displacement reaction with a nitrogen containing aromatic compound which has a nucleophilic side-chain substituent such as CH$_2$SH or CH$_2$NH$_2$. In this displacement reaction, it is the side-chain substituent that is the reacting nucleophile and not the aromatic ring nitrogen. Suitable substrates for this reaction include 2-(mercaptomethyl)pyridine, 2-aminopyridine, 2-(aminomethyl)pyridine or 4-(mercaptomethyl)pyridine. The reaction is carried-out in an inert organic solvent, e.g. methylene chloride, at from about 0° C. to room temperature in the presence of a non-nucleophilic base such as triethylamine or diisopropylethylamine. Quaternization or protonation as described above then gives the Type I.b) cationic substituent. A second suggested synthesis of a Type I.b) cationic substituent starting from a precursor —A-′—OH (e.g. hydroxymethyl) consists of oxidation of the alcohol functionallity to an aldehyde followed by Wittig-type olefination with an appropriate nitrogen-containing aromatic substituted reagent, and finally quaternization. The oxidation may be conveniently accomplished by a Swern oxidation employing oxalyl chloride-dimethylsulfoxide followed by triethylamine. The reaction is conducted in methylene chloride as a solvent at from —70° C. to 0° C. The Wittig reaction is carried-out by reacting the aldehyde with the desired Wittig reagent in a polar solvent such as acetonitrile or dimethylsulfoxide at about room temperature. Suitable Wittig reagents include: pyridylmethylene- triphenylphosphorane, quinolylmethylenetriphenyl- phosphorane and thiazolylmethylenetriphenyl- phosphorane. Quaternization or protonation as described above then completes the synthesis of the Type I.b) cationic substituent. Depending on the particular $R^a$ of Type I.b) that is desired, many other synthesis schemes may be employed, as would be apparent to an organic chemist skilled in the art.

The Type I.c) cationic substituents may be prepared in an analogous manner to that described for I.a) substituents except that the nitrogen containing compound employed in the displacement reaction is an aliphatic amine (i.e. NR$^y$R$^z$R$^w$). However, in cases where the amino group is directly bonded to the naphthalene nucleus (i.e. —A$_p$N+R$^y$R$^z$R$^w$ where p=0) the amine is most conveniently attached to the naphthalene prior to its incorporation into the carbapenem system. If such an amine is primary or secondary, it may require protection with a suitable amine protecting group during the steps employed to attach the naphthalene to the carbapenem. Tertiary amines require no protection and may be quaternized or protonated as described for the Type I.b) cationic substituents.

The Type I.d) cationic substituents are prepared by quaternization or protonation of a non-aromatic ring nitrogen of an appropriate neutral precursor substituent on the naphthalene ring. Quaternization or protonation is accomplished as described above for the Type I.b) substituents. As with the Type I.b) substituents, the neutral precursor may already be attached to the naphthalene ring at the time of its connection to the carbapenem, or the neutral precursor may be elaborated from a simpler precursor substituent on the naphthalene ring after its connection to the carbapenem. Examples of neutral precursor substituents are: —CONH(3-quinuclidinyl), —CONH[4-(N-methylpiperidinyl)], —SO$_2$CH$_2$CH$_2$[2-(N-methylpyrrolidinyl)], —SO$_2$[1-(4-methylpiperazinyl)] and —CH$_2$[1-(4-methylpiperazinyl)]. Elaboration of the neutral precursor substituent from a simpler substituent such as hydroxymethyl may be accomplished in an analogous manner to that described previously for the Type I.b) substituents by employing appropriate reagents to introduce the Type I.d) non-aromatic ring nitrogen moiety which is subsequently to be quaternized or protonated.

Among preferred R$^a$ of Type II are C$_{1-4}$ alkyl monosubstituted with hydroxy, such as, hydroxymethyl; formyl; carboxy, such as, —COOK; carbamoyl, such as, —CONH$_2$; hydroximinomethyl, such as, —CH=NOH or cyano.

In regard to this preferred substitution, the hydroxymethyl may be obtained in any of the positions 1, 5, 6, 7 or 8 of the naphthalene ring by employing the appropriately substituted starting material (i.e. A1 in Flow Sheet A). Thus, proceeding as shown in Flow Sheets A and B, but starting with an "isomeric" A1, a corresponding "isomeric" B3A and a corresponding "isomeric" B4 may be produced.

The preferred formyl substitution on the naphthalene may be obtained from the hydroxymethyl substitution of B4 or isomeric B4 just described by a Swern oxidation. For example, isomeric B4 is oxidized in methylene chloride at from —70° C. to room temperature employing oxalyl chloride-dimethyl sulfoxide, followed by triethylamine, as the active agent. Alternatively, this oxidation may be conveniently accomplished using N-methylmorpholine-N-oxide and a catalytic amount of tetra-n-propylammonium peruthenate in methylene chloride. Obviously, the position of the resultant formyl substitution will depend upon the position of the hydroxymethyl substitution in isomeric B4.

The preferred —CH=NOH substitution on the naphthalene may be conveniently obtained from the formyl substitution just described. This is accomplished simply by exposing the formyl substituted compound to hydroxylamine in an appropriate solvent at room temperature.

The preferred cyano substitution on the naphthalene may be obtained from the —CH=NOH substitution just described. The —CH=NOH substituted compound is dehydrated with triflic anhydride and triethylamine in a solvent at —70° C.

The preferred —COOK substitution on the naphthalene may be obtained from the hydroxymethyl substituted B3A or isomeric B3A described above. For example, an isomeric B3A is oxidized with Jones reagent to convent the hydroxymethyl substituent into a carboxylic acid group. The oxidation with Jones reagent may be incompatible with the carbapenem and thus is optimally performed before ring closure. Prior to ring closure, the carboxy is protected as its allyl ester to permit cyclization of the carbapenem. Protection is carried out by alkylating with allyl bromide and triethylamine. Deprotection following cyclization is carried out with palladium catalyzed deallylation in a solution containing potassium 2-ethylhexanoate as described in McCombie and Jeffrey, *J. Org. Chem.*, 47, 2505 (1983). Deprotection in such a solution yields the desired potassium salt.

The preferred carbamoyl substitution on the naphthalene may be obtained from B3A or "isomeric" B3A by oxidizing the hydroxymethyl with Jones reagent to the corresponding carboxylic acid as described above. This carboxy is converted to —CONH$_2$ by sequentially contacting with 1-ethyl-3-(3-dimethylaminopropyl)carbodiimide hydrochloride, 1-hydroxybenzotriazole, and ammonia in an organic solvent at room temperature. Alternatively, the carboxy may be reacted with 1,1'-carbonyldiimidazole in an aprotic polar solvent, such as tetrahydrofuran followed by treatment with aqueous ammonia to give the same -CONH$_2$. Substituted amides may of course be obtained by replacing ammonia with the corresponding substituted amine. In contrast to the carboxy substitution, this carbamoyl group requires no protection for the conditions of carbapenem cyclization.

Compounds substituted with the preferred R$^a$ of Type II just described may also be obtained by employing the synthesis shown in Flow Sheet C. In this case, the synthetic transformations just described may be carried-out on intermediate C3 prior to attachment of the naphthyl side chain to the carbapenem of on C4 after such attachment.

In addition to or including the above, suitable R$^a$ of Type II include:

| | |
|---|---|
| —OCH$_3$ | —OCH$_2$CO$_2$Na |
| —OCH$_2$CH$_2$OH | —CF$_3$ |
| —F | —Cl |
| —Br | —I |
| —OH | —OCOCH$_3$ |
| —OCONH$_2$ | —SCH$_3$ |
| —SOCH$_3$ | —SO$_2$CH$_3$ |
| —SCH$_2$CH$_2$OH | —SOCH$_2$CH$_2$OH |
| —SO$_2$NH$_2$ | —SO$_2$N(CH$_3$)$_2$ |
| —NHCHO | —NHCOCH$_3$ |
| —NHCO$_2$CH$_3$ | —NHSO$_2$CH$_3$ |
| —CN | —CHO |
| —COCH$_3$ | —COCH$_2$OH |
| —CH=NOH | —CH=NOCH$_3$ |
| —CH=NOCH$_2$CO$_2$H | —CH=NOCMe$_2$CO$_2$H |
| —CH=NOCMe$_2$CO$_2$Me | —CO$_2$CH$_2$CH$_2$OH |
| —CONH$_2$ | —CONHCH$_3$ |
| —CON(CH$_3$)$_2$ | —CONHCH$_2$CN |
| —CONHCH$_2$CONH$_2$ | —CONHCH$_2$CO$_2$H |
| —CONHOH | —CONHOCH$_3$ |
| -tetrazolyl | —CO$_2$Na |
| —SCF$_3$ | —PO$_3$NaH |
| —CONHSO$_2$Ph | —CONHSO$_2$NH$_2$ |
| —SO$_3$Na | —SO$_2$NHCN |
| —SO$_2$NHCONH$_2$ | —CH=CHCN |
| —CH=CHCONH$_2$ | —CH=CHCO$_2$Na |
| —C≡C—CONH$_2$ | —C≡C—CN |
| —CH$_2$OH | —CH$_2$N$_3$ |
| —CH$_2$CO$_2$Na | —SO$_2$CH$_2$CH$_2$OH and —CH$_2$I. |

In the preparation methods described above, the carboxyl group aty the 3-position and the hydroxyl group at the 8-position of the carbapenem remain blocked by protecting groups until the final product is prepared. Suitable hydroxyl protecting groups, P', are silyl groups such as trialkylsilyl. aryl(alkyl)alkoxysilyl, alkloxydiarylsilyl and diarylalkylsilyl and carbonate groups such as alkyloxycarbonyl, substituted alkyloxycarbonyl, benzyloxycarbonyls, substituted benzyloxycarbonyl, allyloxycarbonyl and substitutes allyloxycarbonyl. The preferred protecting groups, in addition to or including those shown in the schemes, are t-butylmethoxyphenylsilyl, t-butoxydiphenylsilyl, trimethylsilyl, triethylsilyl, t-butyldimethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl. Suitable carboxyl protecting groups, M, in addition to or including those shown in the schemes are described hereinbelow.

Deblocking may be carried out in a conventional manner. For compounds prepared according to Flow Sheet B, deprotection may be carried out in a palladium catalyzed reaction in a solution containing potassium 2-ethylhexanoate and 2-ethylhexanoic acid or, alternatively, another suitable nucleophile such as pyrrolidine. Alternatively, for those prepared via Flow Sheet C, deprotection is conducted sequentially. Thus, compound C4 is exposed initially to aqueous acidic conditions, acetic acid or dilute HCl or the like, in an organic solvent such as tetrahydrofuran at 0° C. to ambient temperature for from a few minutes to several hours. The resulting desilylated carbapenem may be isolated by conventional techniques, but is more conveniently taken into the final deprotection process. Thus, addition of an inorganic base such as NaHCO$_3$ or KHCO$_3$ and 10% Pd/C followed by hydrogenation provides for the removal of the p-nitrobenzyl protecting group and the formation of the final compound of Formula I.

The overall molecule must be electronically balanced. Since a quaternary nitrogen is present in the compounds of the present invention, a balancing anion must also, in that case, be present. This is usually accomplished by allowing COOM to be COO$^-$. However, where M is, e.g., a pharmaceutically acceptable ester, a counterion (anion) Z$^-$ must be provided, or alternatively, an anionic substituent might be utilized. A counterion must also be provided or additional anoionic substituent utilized where there is more than one quaternary nitrogen. Further, it is within the scope of this invention to utilize an anionic substituent where the quaternary nitrogen is already balaced by COOM=-COO$^-$. In that case, it will be understood that it is necessary to provide a counterion (cation) for the anionic substituent. However, it is well within the skill of a medicinal chemist, to whom there is available many suitable anionic and cationic counterions, to make such choices.

With reference to the above definitions, "alkyl" means a straight or branched chain aliphatic hydrocarbon radical.

The term "quaternary nitrogen" as used herein refers to a tetravalent cationic nitrogen atom including the cationic nitrogen atom in a tertra-alkylammonium group (e.g. tetramethylammonium, N-methylpyridinium), the cationic nitrogen atom in a protonated ammonium species (e.g. trimethylhydroammonim, N-hydropyridinium), the cationic nitrogen atom in an amine N-oxide (e.g. N-methylmorpholine-N-oxide, pyridine-N-oxide), and the cationic nitrogen atom in an N-amino-ammonium group (e.g. N-aminopyridinium).

The term "heteroatom" means N, S, or O, selected on an independent basis.

The term "heteroaryl" has been defined herein, in relation to the R$^X$ group, to have a specific and limited meaning, being only monocyclic. While the Type I. a) and b) substituents also clearly include heteroaryl groups, being both monocyclic and bicyclic, the term "heteroaryl" has not been used in association with the definitions of those substituents above. It is required that the monocyclic heteroaryl have at least one nitrogen atom, and optionally at most only one additional oxygen or sulfur heteroatom may be present. Heteroaryls of this type are pyrrole and pyridine (one N); and oxazole, thiazole or oxazine (one N plus one O or one S). While additional nitrogen atoms may be present together with the first nitrogen and oxygen or sulfur, giving, e.g., a thiadiazole (two N's plus one S), the preferred heteroaryls are those where only nitrogen heteroatoms are present when there is more than one. Typical of these are pyrazole, imidazole, pyrimidine and pyrazine (two N's) and triazine (three N's).

The heteroaryl group of R$^X$ is always optionally mono-substituted by R$^q$, defined above, and substitution can be on one of the carbon atoms or one of the heteroatoms, although in the latter case certain substituent choices may not be appropriate.

Listed in Table I are specific compounds of the instant invention:

TABLE I

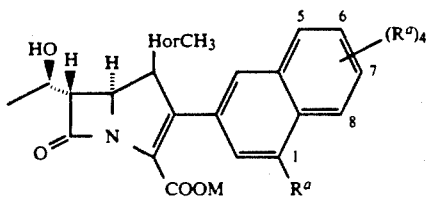

| M | R$^a$ | R$^a$ Position |
|---|---|---|
| (−) | 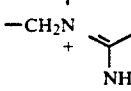 | 1 |
| (−) | 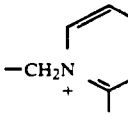 | 5 |
| (−) | 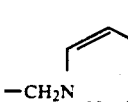 | 6 |
| (−) | 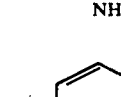 | 7 |
| (−) | 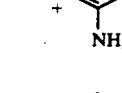 | 8 |
| (−) | 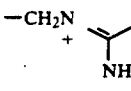 | 1 |
| (−) | 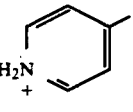 | 5 |

TABLE I-continued
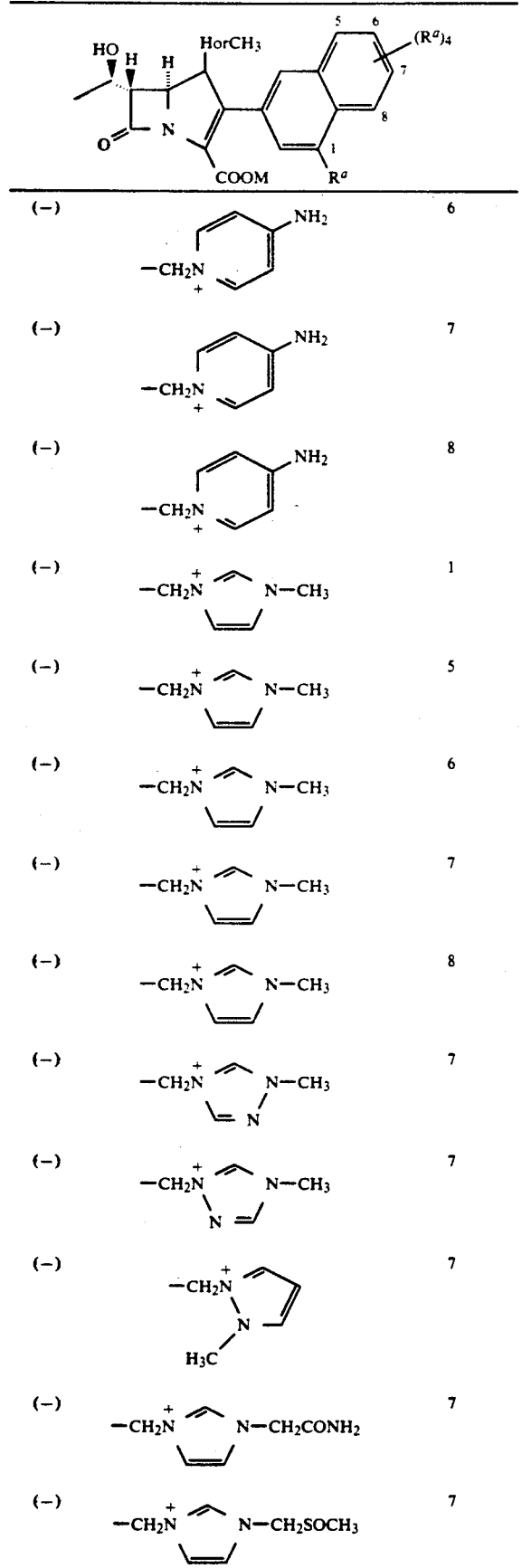
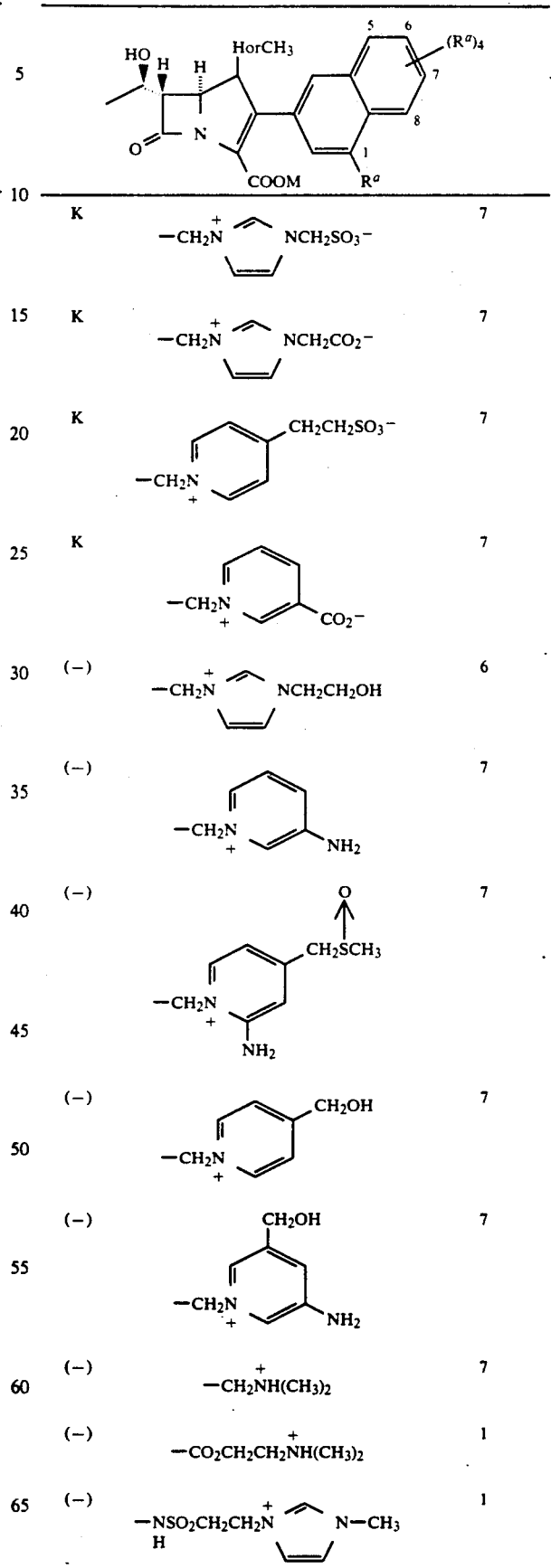

TABLE I-continued

[Structure: bicyclic β-lactam with naphthalene substituent bearing (Rᵃ)₄ at positions 5,6,7,8 and Rᵃ at position 1, COOM group]

| | Rᵃ | n |
|---|---|---|
| (−) | −OCH₂CH₂N⁺(2-aminopyridinium) | 7 |
| (−) | −SCH₂CH₂N⁺(2-aminopyridinium) | 1 |
| (−) | −SO₂CH₂CH₂N⁺(2-aminopyridinium) | 7 |
| (−) | −CH₂OCH₂CH₂N⁺(2-aminopyridinium) | 1 |
| (−) | −CH₂SCH₂CH₂N⁺(2-aminopyridinium) | 1 |
| (−) | −CH₂S(O)(O)N⁺(2-aminopyridinium) | 7 |
| (−) | −CH₂CH₂N⁺(2-aminopyridinium) | 7 |
| (−) | −C(O)CH₂N⁺(2-aminopyridinium) | 7 |
| (−) | −S(O)(OH)NCH₂CH₂N⁺(2-aminopyridinium) | 7 |

TABLE I-continued

[Structure: bicyclic β-lactam with isoquinoline substituent bearing (Rᵃ)₄ at positions 5,6,7,8 and Rᵃ at position 1, COOM group]

| | Rᵃ | n |
|---|---|---|
| (−) | −S(→O)−CH₂CH₂N⁺(imidazolium-N-CH₃) | 1 |
| (−) | −C(O)CH₂N⁺(imidazolium-N-CH₃) | 1 |
| (−) | −S(O)₂CH₂CH₂N⁺(imidazolium-NMe) | 1 |
| (−) | −CH₂S-(1-amino-pyridinium) | 7 |
| (−) | −CH=CH-(N-methylpyridinium) | 7 |
| H | −NH-(2-pyridyl) | 7 |
| (−) | −C(O)NHCH₂-(N-methylpyridinium-2-yl) | 1 |
| (−) | −C(O)NHCH₂CH₂-(N-methylpyridinium-4-yl) | 1 |
| (−) | −S(O)₂N(piperazinium-N,N-diCH₃) | 1 |
| (−) | −S(O)₂CH₂CH₂-(N-methylpyridinium-2-yl) | 1 |

TABLE I-continued

Structure: β-lactam with hydroxyethyl substituent, fused to pyrrolidinone ring with COOM group and naphthyl substituent bearing $(R^a)_4$ groups at positions 5,6,7,8 and $R^a$ at position 1.

| M | $R^{a'}$ | $R^{a'}$ Position |
|---|---|---|
| (−) | −CH₂−(4-pyridinium-N-CH₃, 2-NH₂) | 7 |
| (−) | −CH₂−(4-pyridinium-N-CH₂C(O)NH₂) | 7 |
| K | −C(O)NHCH₂CH₂−(2-pyridinium N-oxide) | 1 |
| K | −SO₂CH₂−(4-pyridinium N-oxide) | 1 |
| (−) | −C(O)NH−(4-piperidinium-N-CH₃) | 1 |
| (−) | N-methyl pyrrolidinium (via CH₂) | 7 |
| (−) | −CH₂−N⁺(CH₃)(morpholine) | 7 |
| (−) | −CH₂−N⁺(CH₃)₃ | 7 |
| (−) | −CH₂−(quinuclidinium) | 7 |
| K | −CH₂−N⁺(quinuclidinium-CO₂⁻) | 7 |
| K | −CH₂−N⁺(morpholine N-oxide) | 7 |

TABLE I-continued

Structure: same core β-lactam / naphthyl system.

| M | $R^{a'}$ | $R^{a'}$ Position |
|---|---|---|
| (−) | −CH₂−N⁺(piperidine N-oxide) | 7 |
| (−) | −C(O)NH−CH₂−(4-piperidinium-N,N-diCH₃) | 1 |
| (−) | CN | 1 |
| (−) | SOCH₃ | 1 |
| (−) | CO₂K | 1 |
| (−) | CO₂K | 1 |
| (−) | tetrazole-NK | 1 |
| (−) | tetrazole-NK | 1 |
| (−) | SO₃K | 1 |
| (−) | CO₂K | 1 |
| (−) | SO₃K | 1 |
| (−) | SO₃K | 5 |
| (−) | CHO | 1 |

| M | $R^{a'}$ | $R^{a'}$ Position |
|---|---|---|
| (−) | −CH₂N⁺(imidazole-NCH₃) | 7 |
| (−) | −CH₂N⁺(imidazole-NCH₃) | 7 |
| (−) | −CH₂N⁺(imidazole-NCH₃) | 7 |
| (−) | −CH₂N⁺(2-aminopyridinium) | 7 |
| (−) | −CH₂N⁺(2-aminopyridinium) | 7 |
| (−) | −CH₂N⁺(4-aminopyridinium) | 7 |

TABLE I-continued

| | | |
|---|---|---|
| (−) | −CH₂N⁺(pyridinyl-NH₂) | 7 |
| (−) | N⁺-CH₃ (pyrrolidinyl) | 7 |
| (−) | −CH₂−N⁺(CH₃)(pyrrolidinyl) | 6 |
| (−) | −CH₂−N⁺(CH₃)(pyrrolidinyl) | 7 |
| (−) | −CH₂N⁺(pyridinyl-NH₂) | 7 |

The carbapenem compounds of the present invention are useful per se and in their pharmaceutically acceptable salt and ester forms in the treatment of bacterial infections in animal and human subjects. The term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above may also include non-toxic acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanaoate, hexanoate, hydrochloride, hydrobromide, hydroiodide, 2-hydroxyethanesulfonate, lactate, maleate, methanesulfonate, 2-naphthalene-sulfonate, nicotinate, oxalate, pamoate, pectinate, persulfate, 3-phenylpropionate, picrate, pivalate, propionate, succinate, tartrate, thiocyanate, tosylate, and undecanoate.

The pharmaceutical acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Broadly, such ester protecting groups include alkyl, substituted alkyl, benzyl, substituted benzyl, aryl, substituted aryl, allyl, substituted allyl and triorganosilyl. Examples of specific such ester protecting groups include benzhydryl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, o-nitrobenzyl, p-methoxyphenyl, 4-pyridylmethyl and t-butyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the anti-bacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10–60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5–50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5–25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occuring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Application No. 79102616.4 filed Jul. 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1.) define the procedure for determining DHP susceptibility of the present carbapenems and 2.) disclose suitable inhibitors, combination compositions and methods of treatment, they are incorporated herein by reference. A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

The invention is further defined by reference to the following examples, which are intended to be illustrative and not limiting. All temperatures are in degrees Celsius.

EXAMPLE 1

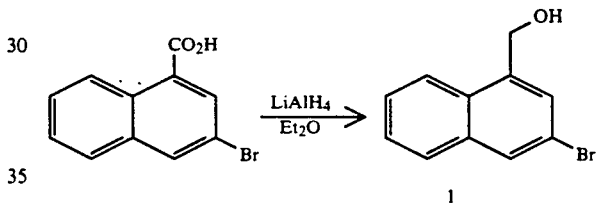

3-Bromo-1-(hydroxymethyl)napthalene (1)

To a stirred solution of 1.0 g (3.98 mmoles) of 3-bromo-1-naphthoic acid in 38 ml of anhydrous diethyl ether was added dropwise a 0.86M lithium aluminum hydride in diethyl ether solution (44 ml, 3.78 mmoles). The resulting slurry was stirred at reflux under a $N_2$ atmosphere for 3 hours. The slurry was cooled to rt and moist $Na_2SO_4$ was added. The resulting slurry was filtered through a $MgSO_4$ plug and the filtrate concentrated under vacuum to provide 782.7 mg of white residue. Purification on silica gel plates which were eluted with $CH_2Cl_2$ gave 722.3 mg of 3-bromo-1-(hydroxymethyl)naphthalene as a white crystalline solid.

$^1$H-NMR (300 MHz, CDCl$_3$): δ1.79 (bs, CH$_2$OH), 5.15 (s, CH$_2$OH), 7.54 (m, naphthyl-H6 and H7), 7.66 (s, naphthyl-H2), 7.79 (m, naphthyl-H5), 7.97 (s, naphthyl-H4), 8.03 ppm (m, naphthyl-H8).

IR (CH$_2$Cl$_2$): 3605 cm$^{-1}$.

EXAMPLE 2

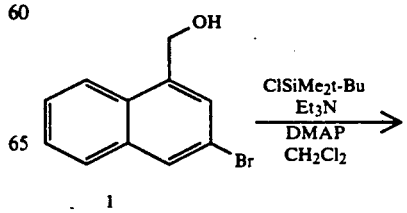

-continued

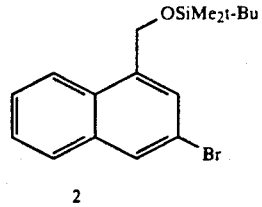

3-Bromo-1-(t-butyldimethylsilyloxymethyl)naphthalene (2)

To a solution of 1.49 g (6.3 mmoles) of 3-bromo-1-(hydroxymethyl)-naphthalene in 25 ml anhydrous CH$_2$Cl$_2$ were added sequentially N,N-dimethyl-4-aminopyridine (76.8 mg, 0.63 mmoles), t-butyldimethylchlorosilane (1.23 g, 8.2 mmoles) and triethylamine (1.22 ml, 8.8 mmoles). The resulting solution was stirred at room temperature for 2 hours under a N$_2$ atmosphere and then partitioned between EtOAc and ice/H$_2$O. The organic phase was separated, washed with brine, dried with anhydrous Na$_2$SO$_4$, filtered and concentrated under vacuum to provide a pale yellow liquid. The crude reaction residue was purified by column chromatography (44 g silica gel, packed and eluted with 9:1 hexanes: CH$_2$Cl$_2$) to provide 2.19 g of the title compound as a clear liquid.

$^1$H-NMR (200 MHz, CDCl$_3$): δ0.15 (s, C$\underline{H}_3$Si), 0.97 (s, (C$\underline{H}_3$)$_3$CSi), 5.17 (s, C$\underline{H}_2$O), 7.22–7.95 ppm (m, ArH).

of 1,2-dibromoethane was added close to the magnesium surface. Heat was applied to initiate the reaction and the mixture then stirred at 30° under a N$_2$ atmosphere for 2.5 hours. At the end of this time the heat was removed and the yellow Grignard solution was employed as described below.

To a solution of 2.11 g (3.0 mmoles) of (3S,4R)-1-(allyloxycarbonyltriphenylphosphorylidene)methyl-3-[(R)-1-(allyloxycarbonyloxy)ethyl]-4-[(2-pyridylthio)-carbonyl]methyl-azetidin-2-one, 3, in 20 ml anhydrous tetrahydrofuran at −90° under a N$_2$ atmosphere was added 11.5 ml (ca. 4.6 mmoles) of the above Grignard solution. The reaction solution was stirred at −9° under a N$_2$ atmosphere for 50 minutes and then 10 ml of saturated aqueous ammonium chloride solution was added. The resulting mixture was partitioned between EtOAc and ice/H$_2$O. The organic phase was separated and washed twice with ice/5N aqueous NaOH solution. The organic phase was then washed with brine, dried with anhydrous Na$_2$SO$_4$, filtered and concentrated under vacuum to provide 3.09 g of a yellow foam. The crude reaction residue was purified by column chromatography (150 g silica gel; packed and eluted with 3:2; hexanes: EtOAc) to provide 2.24 g of the title compound as a pale yellow foam.

IR (CH$_2$Cl$_2$): 1745, 1680, 1615 cm$^{-1}$; 300 MHz $^1$H-NMR (CDCl$_3$): inter alia δ0.15 (s, C$\underline{H}_3$Si), 0.96 (s, (C$\underline{H}_3$)$_3$CSi), 1.18 (d, J=6.9 Hz, C$\underline{H}_3$CHCH), 5.18 ppm (s, naphthyl-C$\underline{H}_2$).

EXAMPLE 3

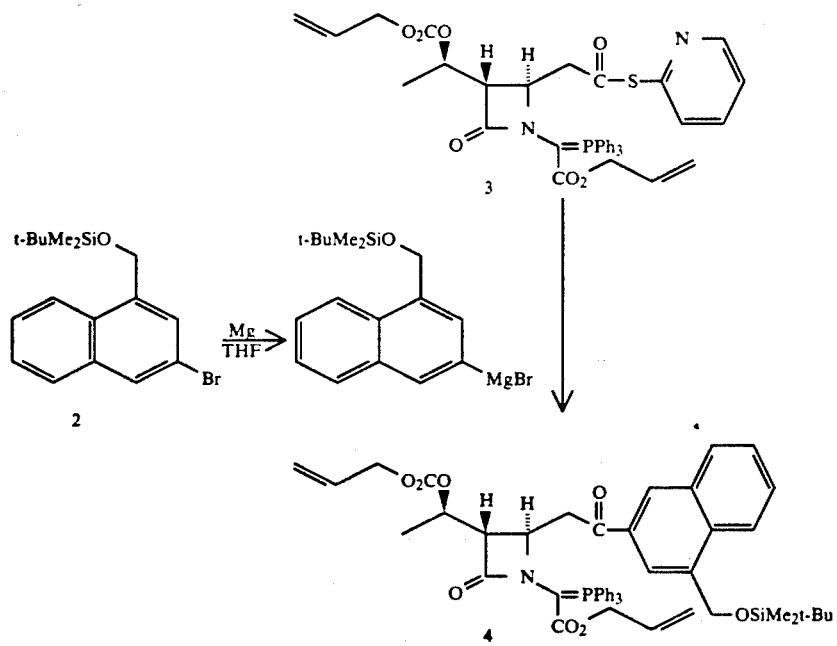

(3S,4R)-1-(Allyloxycarbonyl-triphenylphosphoranylidene)methyl-3-[1R-(allyloxycarbonyloxy)ethyl]-4-[1-(t-butyldimethylsilyloxymethyl)-3-naphthylcarbonyl]methyl-azetidin-2-one (4)

To a mixture of magnesium turnings (160 mg, 6.6 mmoles) in 15 ml anhydrous THF was added the bromo-naphthalene 2 prepared in the previous example (2.09 g, 6.0 mmoles). The stirring was stopped and 35 μl

EXAMPLE 4

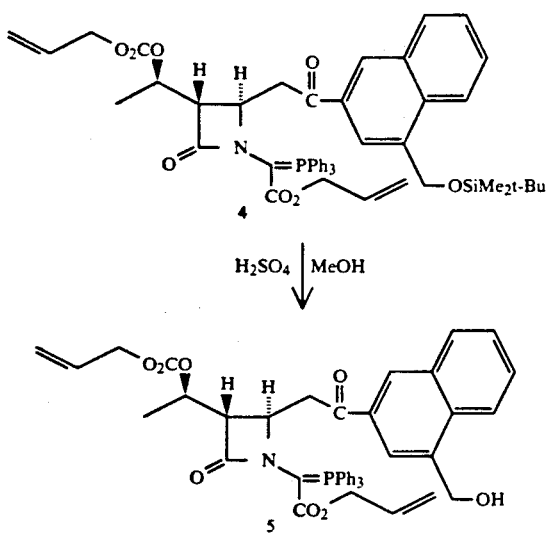

(3S,4R)-1-(allyloxycarbonyltriphenylphosphoranylidene)methyl-3-[1R-(allyloxycarbonyloxy)ethyl]-4-[1-(hydroxymethyl)-3-naphthylcarbonyl]methyl-azetidin-2-one (5)

To a solution of 2.9 g (3.32 mmoles) of azetidinone 4 in 35 ml anhydrous MeOH at 0° under a N₂ atmosphere was added a 0.75M methanolic sulfuric acid solution (6.64 ml, 4.98 mmoles). The resulting solution was stirred 1.5 hrs. at 0° and then was concentrated under vacuum to 15 ml volume. The solution was then partitioned between EtOAc and ice/H₂O/saturated aqueous bicarbonate. The organic phase was separated and washed with brine, dried with anhydrous Na₂SO₄, filtered and concentrated under vacuum to provide 2.50 g of the title compound as a yellow foam.

¹H-NMR (300 MHz, CDCl₃): inter alia δ1.17 ppm (d, J=6.8 Hz, CH₃CHCH).

IR (CH₂Cl₂): 3600, 1745, 1680, 1620 cm⁻¹.

EXAMPLE 5

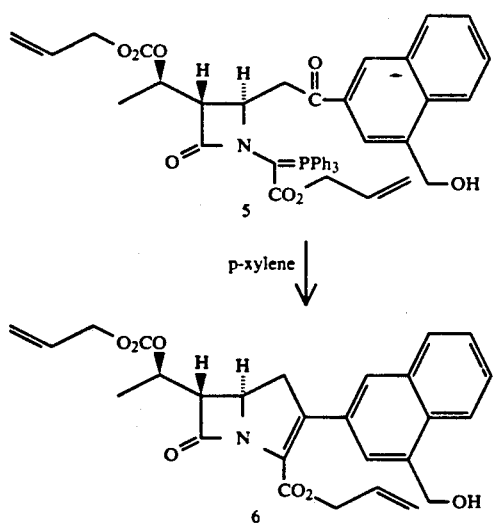

Ally-(5R,6S)-2-(1-hydroxymethyl-3-naphthyl)-6-[1R-(allyloxycarbonyloxy)ethyl]-carbapen-2-em-3-carboxylate (6)

To solution of 2.5 g (3.3 mmoles) of azetidinone 5 in 300 ml anhydrous xylenes at room temperature under an argon atmosphere was added several crystals of hydroquinone. The solution was stirred 2 hours at 155° under an argon atmosphere and then cooled to room temperature. The solution was concentrated under vaccum to a yellow paste and the crude product purified by column chromatography (45 g silica gel; packed and eluted with 3:2; hexanes:EtOAc) to provide 1.28 g of the title compound.

¹H-NMR (300 Mz, CDCl₃): δ1.49 (d, J=5.8 Hz, CH₃CH), 1.96 (t, CH₂OH), 3.3 (dd, J=10.0, 18.1 Hz, CHCH₂C), 3.42 (m, CHCH₂C and CHCHC=O) 4.31 (dt, J=4.4, 7.8 Hz, CHCHCH₂), 4.67 (m, CH₃CHCH and CH₂CH=CH₂), 5.12 (d, J=5.4 Hz, CH₂OH), 5.29 (m, CH₂CH=CH₂), 5.90 (m, CH₂CH=CH₂), 7.54 (m, naphthyl-H2, H6, H7) 7.78 (s, naphthyl-H4), 7.84 (dd, J=1.7, 8.4 Hz, naphthyl-H5), 8.05 ppm (d, J=8.6 Hz, naphthyl-H8);

IR (CH₂Cl₂): 1780, 1745, 1720 cm⁻¹; UV(dioxane): λ_max=288, 325 nm.

EXAMPLE 6

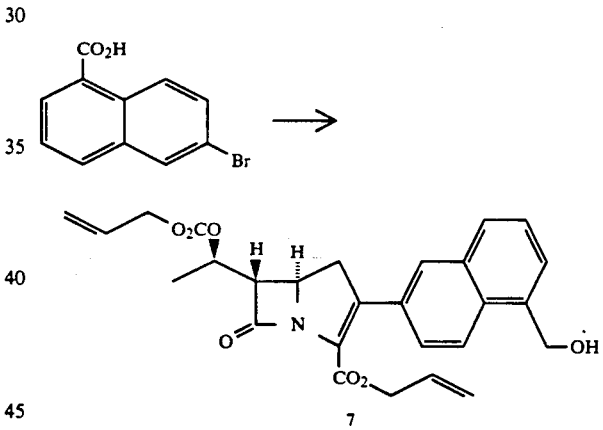

Allyl-(5R,6S)-2-(1-hydroxymethyl-6-naphthyl)-6-[1R-(allyloxycarbonyloxy)ethyl]-carbapen-2-em-3-carboxylate (7)

In an analogous manner to that described in Examples 1-5, but starting with 6-bromo-1-naphthoic acid [M. J. S. Dewar and P. J. Grisdale, J. Amer. Chem. Soc. 84, 3541 (1962)], the title compound was obtained as a pale yellow foam.

¹H-NMR (300 MHz, CDCl₃): δ1.47 (d, J=6.35 Hz, 3H, CH₃), 3.25 (dd, J=9.8, 18.1 Hz, 1H, H1a), 3.37 (dd, J=9.0, 18.1 Hz, 1H, H1b), 3.42 (dd, J=8.2, 2.8 Hz, 1H, H5), 4.28 (dt, J=2.8, 9.4 Hz, 1H, H6), 4.55-4.75 (m, 4H, —OCH₂C=C), 5.08 (bs, 2H, ArCH₂O), 5.1-5.4 (m, 5H, H8, —C=CH₂), 5.75-6.0 (m, 2H, —CH=C), 7.4-7.55 (m, 3H, ArH), 7.79 (d, J=10.9 Hz, 1H, ArH), 7.83 (s, 1H, ArH), 8.04 ppm (d, J=8.79, 1H, ArH), IR (CHCl₃): 3610 (OH), 1780 (β-lactam), 1745 (carbonate), 1725 cm⁻¹ (ester).

FAB-MS: m/e=478 (M+H).

EXAMPLE 7

Allyl-(5R,6S)-2-(2-hydroxymethyl-6-naphthyl)-6-[1R-(allyloxycarbonyloxy)ethyl]-carbapen-2-em-3-carboxylate (8)

In analogous manner to that described in Examples 1-5, but starting with 6-bromo-2-naphthoic acid [L. G. Anderson and D. Johnston, J. Amer. Chem. Soc. 65, 239 (1943)], the title compound was obtained as a white foam.

$^1$H-NMR (300 MHz, CDCl$_3$): δ1.50 (d, J=6.77 Hz, 3H, CH$_3$), 3.25-3.55 (m, 2H, H1), 3.45 (dd, J=13.2, 2.7 Hz, 1H, H6), 4.32 (dt, J=2.7, 9.5 Hz, 1H, H5), 4.55-475 (m, 4H, —OCH$_2$C=C), 4.86 (d, J=5.37, 2H, ArCH$_2$O), 5.1-5.4 (m, 5H, H8, —C=CH$_2$), 5.75-6.0 (m, 2H, —CH=C), 7.4-7.5 (m, 2H, ArH), 7.7-7.85 ppm (m, 4H, ArH).

IR (CHCl$_3$): 3600 (OH), 1780 (β-lactam), 1745 (carbonate), 1725 cm$^{-1}$ (ester).

FAB-MS: m/e=478 (M+H).

EXAMPLE 8

Allyl-(5R,6S)-2-(2-hydroxymethyl-7-naphthyl)-6-[1R-(allyloxycarbonyloxy)ethyl]-carbapen-2-em-3-carboxylate (9)

In a analogous manner to that described in Examples 1-5, but starting with 7-bromo-2-naphthoic acid [W. Adcock and P. R. Wells, Aust. J. Chem. 18, 1351 (1965)], the title compound was obtained as a pale yellow foam.

$^1$H-NMR (300 MHz, CDCl$_3$): δ1.49 (d, J=6.35 Hz, 3H, CH$_3$), 3.28 (dd, J=9.9, 18.1 Hz, 1H, H1a), 3.39 (dd, J=8.9, 18.1 Hz, 1H, H1b), 3.44 (dd, J=8.4, 2.8 Hz, 1H, H6), 4.32 (dt, J=2.8, 9.3 Hz, 1H, H5), 4.55-4.75 (m, 4H, —OCH$_2$C=C), 4.85 (d, J=5.62 Hz, 2H, ArCH$_2$O), 5.1-5.4 (m, 5H, H8, —C=CH$_2$), 5.75-6.0 (m, 2H, —CH=C), 7.4-7.55 (m, 2H, ArH), 7.75-7.85 ppm (m, 4H, ArH).

IR(CHCl$_3$): 3600 (OH), 1780 (β-lactam), 1745 (carbonate), 1725 cm$^{-1}$ (ester).

EXAMPLE 9

Allyl-(5R,6S)-2-(1-hydroxymethyl-7-naphthyl)-6-[1R-(allyloxycarbonyloxy)ethyl]-carbapen-2-em-3-carboxylate (10)

In analogous manner to that described in Examples 1-5, but starting with 7-bromo-1-naphthoic acid [H. Goldstein and H. A. Fischer, Helv. Chim. Acta 21, 1519 (1938)], the title compound was obtained as a white foam.

$^1$H-NMR (300 MHz, CDCl$_3$): δ1.51 (d, J=6.35 Hz, 3H, CH$_3$), 3.3-3.5 (m, 2H, H1), 3.45 (dd, J=9.1, 2.8 Hz, 1H, H6), 4.33 (dt, J=2.8, 9.9 Hz, 1H, H5), 4.55-4.75 (m, 4H, —OCH$_2$C=C), 5.1 (d, J=6.25 Hz, 2H, ArCH$_2$O), 5.1-5.4 (m, 5H, H8, —C=CH$_2$), 5.75-6.0 (m, 2H, —CH=C), 7.4-7.55 (m, 3H, ArH), 7.75-7.85 (m, 2H, ArH), 8.20 ppm (s, 1H, ArH).

IR (CHCl$_3$): 3610 (OH), 1780 (β-lactam), 1745 (carbonate) 1725 cm$^{-1}$ (ester).

FAB-MS: m/e=478 (M+H).

EXAMPLE 10

2-Trimethylstannyl-6-hydroxymethylnaphthalene (12)

Bromonaphthalene 11 (1.72 g, 4.9 mmol), prepared in analogous manner to that described in Examples 1 and 2, but starting with 6-bromo-2-naphthoic acid, was dissolved in anhydrous THF (30 mL) and cooled to −78° C. under nitrogen. To this stirred solution was added a 1.7M solution of t-BuLi in pentane (2.2 equiv.; 10.8 mmol; 6.3 mL). After 2.5 hours at −78° C., Me$_3$SnCl (1.2 equiv.; 5.88 mmol; 1.17 g) was added as a solid. The cold bath was removed and the reaction allowed to reach ambient temperature. After 4 hours, the reaction was quenched with water. The solvent was removed in vacuo and the residual dissolved in Et$_2$O. Washing with water and brine was followed by drying over MgSO$_4$, filtering and removal of solvent. The residual was dissolved in anhydrous THF and treated with a 1.0M solution of nBu$_4$NF in THF (1.1 equiv.; 5.4 mmol; 5.4 mL) at ambient temperature for 5 minutes. Quenching the reaction with saturated NH$_4$Cl was followed by removal of the solvent in vacuo. The residual was dissolved in EtOAc and washed with water and brine, dried with magnesium sulfate, filtered and the solvent removed in vacuo. Purification by flash chromatography (30% EtOAc in hexanes) and crystallization from Et$_2$O/hexanes at 0° provided 1.38 g (87%) of stannyl alcohol as a white solid.

$^1$H-NMR (300 MHz, CDCl$_3$): δ0.34 (s, 9H), 1,69 (t, J=5.5 Hz, 1H), 4.85 (d, J=6.0 Hz, 2H), 7.46 (dd, J=8.5, 1.5 Hz, 1H), 7.57 (d, J=8.5 Hz, 1H), 7.75–7.81 (m, 3H), 7.94 ppm (s, 1H).

EXAMPLE 11

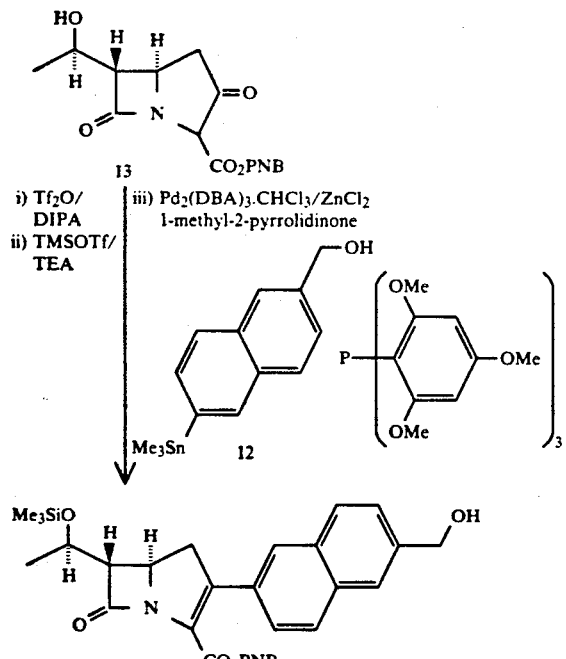

p-Nitrobenzyl-(5R,6S)-2-(2-hydroxymethyl-6-naphthyl)-6-[1R-(trimethylsilyloxy)ethyl]-carbapen-2-em-3-carboxylate (14)

A dry 15 mL receiving flask was charged with the bicyclic β-ketoester 13 (143 mg; 0.41 mmol) and a magnetic stir bar and the system was purged with nitrogen. Two mL of anhydrous tetrahydrofuran (THF) was added and upon dissolution of 13, the reaction vessel was cooled to −78° C. under N$_2$. Diisopropylamine (0.063 mL, 0.45 mmol) was then added and the stirring was continued for 10 minutes. Trifluoromethanesulfonic anhydride (0.075 mL, 0.45 mmol) was added, followed by stirring for additional 15 minutes. Triethylamine (0.062 mL, 0.45 mmol) was then added, followed by trimethylsilyl trifluoromethanesulfonate (0.087 mL, 0.45 mmol).

While the above reaction was stirred for 20 minutes, the organostannane 12 (144 mg, 0.45 mmol), tris(dibenzylideneacetone)dipalladium-chloroform (8.5 mg, 0.0082 mmol) and tris(2,4,6-trimethoxyphenyl)phosphine (17.4 mg, 0.033 mmol) were weighed into a single vial and the vial was purged with nitrogen. When the above reaction time had elapsed, N-methylpyrrolidinone (2 mL) was added to the initial reaction mixture followed by the previously weighed solids. A 0.87M zinc chloride in ether solution (0.52 mL, 0.45 mmol) was then added. The low temperature bath was then removed and the reaction vessel was placed in a luke warm water bath to allow it to quickly reach ambient temperature. After reaching ambient temperature, the mixture was stirred for 15 minutes. The reaction was then quenched by pouring the contents of the flask into a 125 mL separatory funnel containing diethyl ether, ethyl acetate and water. The organic phase was separated and washed with water and brine. The organic phase was dried over magnesium sulfate. The mixture was then filtered and the solvent removed under vacuum. Flash column chromatography of the residue (silica gel, 40% ethyl acetate/hexanes) provided 123 mg (54%) of the desired carbapenem.

$^1$H—NMR (300 MHz, CDCl$_3$): δ0.14 (s, 9H), 1.30 (d, J=6.2 Hz, 3H), 1.89 (dd, J$_1$=J$_2$=6.1 Hz, 1H), 3.22–3.44 (complex m, 3H), 4.23–4.34 (complex m, 2H), 4.85 (d, J=6.1 Hz, 2H), 5.20 (ABq, J$_{AB}$=13.7 Hz, Δv$_{AB}$=54.5 Hz, 2H), 7.21 (d, J=8.7 Hz, 2H), 7.38 (dd, J=8.6, 1.7 Hz, 1H), 7.44 (dd, J=8.4, 1.6 Hz, 1H), 7.66–7.76 (complex m, 4H), 7.88 ppm (d, J=8.7 Hz, 2H).

IR (CHCl$_3$): 3600(w), 1770(s), 1720(m), 1600(m), 1520(s) cm$^{-1}$.

UV (CH$_3$CN): λ$_{max}$=320, ε=5000; λ$_{max}$=270, ε=7200

EXAMPLE 12

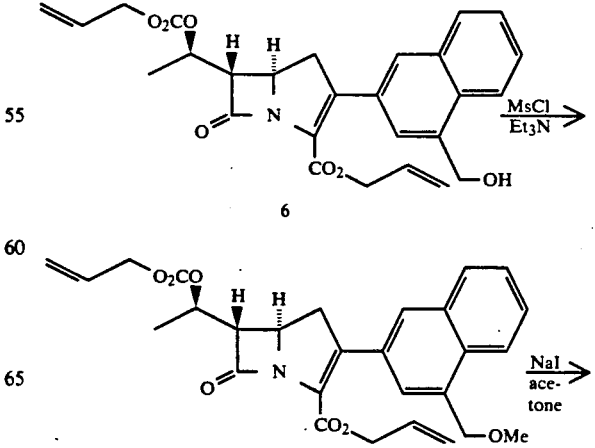

-continued

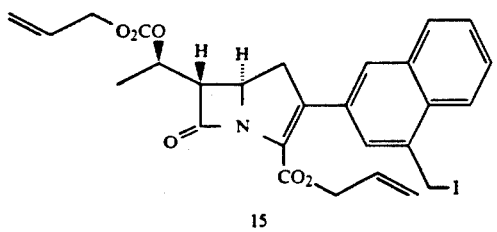

Allyl-(5R,6S)-2-(1-iodomethyl-3-naphthyl)-6-[1R-(allyloxycarbonyloxy)ethyl]-carbapen-2-em-3-carboxylate (15)

To a solution of 107.0 mg (0.225 mmoles) of carbapenem 6 in 4 ml anhydrous $CH_2Cl_2$ at $-20°$ C. under a $N_2$ atmosphere was added triethylamine (50.1 μl, 0.36 mmoles), followed by mesyl chloride (22.7 μl, 0.29 mmoles). The resulting solution was stirred at $-20°$ under $N_2$ atmosphere for 30 minutes. And then partitioned between $CH_2Cl_2$ and ice/2.0N aqueous HCl solution. The organic phase was separated and washed with brine, dried with anhydrous $Na_2SO_4$, filtered and concentrated under vacuum to provide 154.5 mg of a clear film.

$^1$H—NMR (300 MHz, $CDCl_3$): δ2.88 (s, C$\underline{H}_3SO_2$), 5.68 (s, C$\underline{H}_2OSO_2$).

The crude reaction residue was dissolved in 4 ml anhydrous acetone and sodium iodide (67.5 mg, 0.45 mmoles) was added to the resulting solution. The solution was stirred at room temperature for 1.5 hrs and then partitioned between $CH_2Cl_2$ and ice/0.5M aqueous $Na_2S_2O_3$ solution. The organic phase was separated and washed with brine, dried with anhydrous $Na_2SO_4$, filtered and concentrated under vacuum to provide a yellow film. The crude reaction residue was purified by thin layer chromatography (2×1000μ 20×20 cm silica gel, eluted with 4% EtOAc in $CH_2Cl_2$) to provide 128.4 mg of the title compound as a yellow foam.

$^1$H—NMR (300 MHz $CDCl_3$): δ1.51 (d, J=6.8 Hz, C$\underline{H}_3$CHCH), 3.31 (dd, J=9.9, 18.2 Hz, C$\underline{H}_2$CHCH), 3.41 (dd, J=8.7, 18.1 Hz, C$\underline{H}_2$CHCH), 3.46 (dd, J=2.7, 8.2 Hz, C$\underline{H}_2$CHCH), 4.33 (dt, J=2.8, 9.2 Hz CHC$\underline{H}$CH$_2$), 4.70 (m, $CH_2CH$=$CH_2$ and CH$_3$C$\underline{H}$CH), 4.87 (s, naphthyl-C$\underline{H}_2$I), 5.3 (m, CH$_2$CH=C$\underline{H}_2$), 5.91 (m, CH$_2$C$\underline{H}$=CH$_2$), 7.43 (t, J=7.1, 7.7 Hz, naphthyl-$\underline{H}$6), 7.59 (d, J=1.7 Hz, naphthyl-$\underline{H}$1), 7.67 (t, J=7.0, 7.1 Hz, naphthyl-$\underline{H}$7), 7.80 (s, naphthyl-$\underline{H}$4); 7.76 (d, J=8.2 Hz, naphthyl-$\underline{H}$5), 8.07 ppm (d, J=8.1 Hz, naphthyl-$\underline{H}$8).

IR ($CH_2Cl_2$): 1780, 1745, 1720 cm$^{-1}$.

EXAMPLE 13

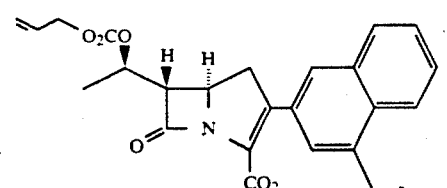

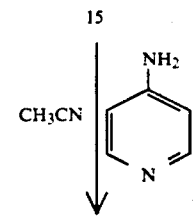

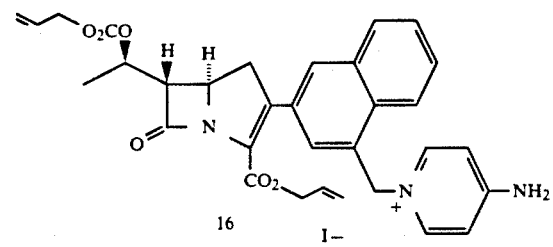

Allyl-(5R,6S)-2-(1-(4-aminopyridinium)methyl-3-naphthyl)-6-[1R-(allyloxycarbonyloxy)ethyl[-1-carbapen-2-em-3-carboxylate iodide. (16).

To a stirred solution of 58.1 mg (0.099 mmoles) of the iodide 15 in 2 ml anhydrous acetonitrile at 0° C. under a $N_2$ atmosphere was added 11.2 mg (0.12 mmoles) of 4-aminopyridine as a solid. The resulting reaction solution was stirred at room temperature under a $N_2$ atmosphere for 18 hours and then was partitioned between $CH_2Cl_2$ and ice/$H_2O$. The organic layer was separated, dried with anhydrous $Na_2SO_4$, filtered and concentrated under vacuum to provide 62.9 mg of a yellow film. The residue was dissolved in $CH_2Cl_2$ and the solution diluted with diethyl ether. The gummy solid which separated was collected and redissolved in $CH_2Cl_2$. Ether was again added and the resulting solid was collected and dried under vacuum to provide 64.3 mg of the title compound as an orange foam.

$^1$H—NMR (300 MHz, $CDCl_3$): δ1.47 (d, J=6.77 Hz, C$\underline{H}_3$CHCH), 3.37 (dd, J=9.9, 16.0 Hz, CHC$\underline{H}_2$C), 3.57 (m, CHC$\underline{H}_2$C and CHC$\underline{H}$C=O), 4.39 (dt, J=2.1, 9.5 Hz, CHCHC$\underline{H}_2$), 4.32 (m, CH$_3$C$\underline{H}$CH, C$\underline{H}_2$CH=CH$_2$), 5.25 (m, CH$_2$CH=C$\underline{H}_2$), 5.80 (s, naphthyl-C$\underline{H}_2$), 5.88 (m, CH$_2$C$\underline{H}$=CH$_2$), 7.18 (d, J=7.1 Hz, pyridine $\underline{H}$3 and $\underline{H}$5), 7.53 (m, naphthyl-$\underline{H}$), 7.70 (s, naphthyl-$\underline{H}$), 7.85 (d, J=8.2 Hz, naphthyl-$\underline{H}$), 7.87 (d, J=7.7 Hz, naphthyl-$\underline{H}$), 8.05 ppm (d, J=6.3 Hz, pyridine $\underline{H}$2 and $\underline{H}$6);

IR ($CH_2Cl_2$): 1780, 1745, 1720, 1655 cm$^{-1}$;

UV(dioxane): $\lambda_{max}$=285 nm.

EXAMPLE 14

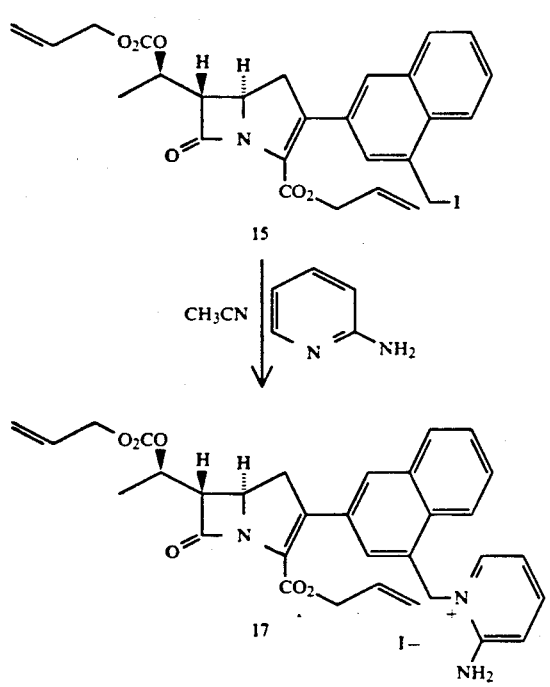

Allyl-(5R,6S)-2-[1-(2-aminopyridinium)methyl-3-naphthyl]-6-[1R-(allyloxycarbonyloxy)ethyl]-1-carbapen-2-em-3-carboxylate iodide (17)

To a solution of iodide 15 (67.0 mg, 0.115 mmol) in 2 ml of acetontrile was added 2-aminopyridine (21.5 mg, 0.229 mmol) in one portion. After stirring at room temperature for 18 hours, the mixture was diluted with methylene chloride and washed successively with water and brine. Drying (MgSO$_4$) and evaporation left a solid which was dissolved in a minimum volume of methylene chloride. The product was precipitated by the addition of ethyl ether and was isolated by centrifugation. Drying in vacuo yielded 28.5 mg (45%) of the title compound as a tan solid.

$^1$H—NMR (300 MHz, CDCl$_3$): δ1.48 (d, J=5.86 Hz, 3H, CH$_3$), 3.30-3.55 (m, 2H, H1), 3.54 (dd, J=7.8, 2.7 Hz, H6), 4.35 (dt, J=2.7, 9.5 Hz, 1H, H5), 4.55-4.75 (m, 4H, —OCH$_2$C=C), 5.1-5.4 (m, 5H, H8, —C=CH$_2$), 5.75-6.0 (m, 2H, —CH=C), 5.92 (bs, 2H, —CH$_2$N), 6.66 (t, J=6.3, 1H, ArH), 7.35-7.95 ppm (m, 9H, ArH).

IR (CHCl$_3$): 1780 (β-lactam), 1745 (carbonate), 1720 (ester), 1665 cm$^{-1}$ (iminium).

FAB-MS: m/e=554 (M+H).

EXAMPLE 15

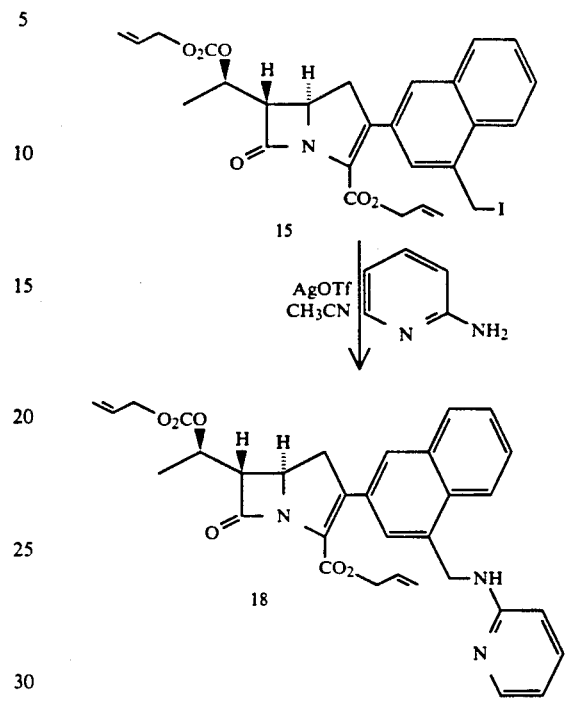

Allyl-(5R,6S)-2-{1-[(2-pyridyl)amino]methyl-3-naphthyl}-6-[1R-(allyloxycarbonyloxy)ethyl]-1-carbapen-2-em-3-carboxylate (18)

To a solution of iodide 15 (46.0 mg, 0.0786 mmol) in 2 ml of acetonitrile was added 2-aminopyridine (9.6 mg, 0.10 mmol) and silver trifluoromethanesulfonate (32 mg, 0.13 mmol) and the mixture was stirred at room temperature. After 16 hours, the reaction mixture was diluted with methylene chloride and filtered. The filtrate was washed successively with water, sat. NH$_4$Cl, sat. NaHCO$_3$, and brine. Drying (MgSO$_4$) and evaporation left an oil which was purified by preparative TLC on silica gel (1:4 EtOAc/CH$_2$Cl$_2$) to yield 13 mg (24%) of the title compound as an oil.

$^1$H—NMR (300 MHz, CDCl$_3$): δ1.50 (d, J=6.95 Hz, 3H, CH$_3$), 3.20-3.45 (m, 2H, H1), 3.44 (dd, J=8.1, 2.8 Hz, 1H, H6), 4.31 (dt, J=2.8, 9.4 Hz, 1H, H5), 4.55-4.75 (m, 4H, —OCH$_2$C=C), 4.94 (s, 2H, —CH$_2$N), 5.1-5.4 (m, 5H, H8, —C=CH$_2$), 5.75-6.0 (m, 2H, —CH=C), 6.43 (d, J=7.9 Hz, 1H, PyH), 6.64 (dd, J=7.1, 5.0 Hz, 1H, PyH), 7.44 (dd, J=7.9, 7.1 Hz, 1H, PyH), 7.5-8.1 (m, 6H, ArH), 8.15 ppm (br d, J=5 Hz, 1H, PyH).

IR (CHCl$_3$): 3440 (NH), 1780 (β-lactam), 1745 (carbonate), 1725 cm$^{-1}$ (ester).

EXAMPLE 16

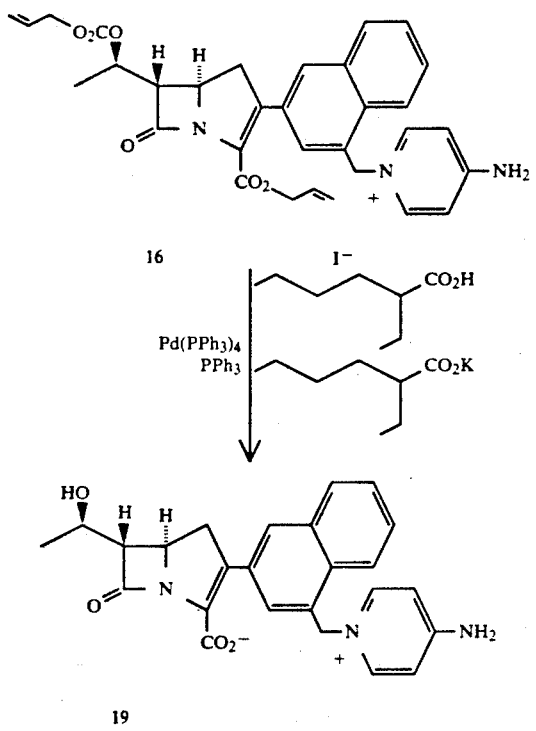

(5R,6S)-2-(1-(4-Aminopyridinium)methyl-3-naphthyl)-6-[1R-hydroxyethyl]-carbapen-2-em-3-carboxylate. (19)

To a stirred solution of 64.3 mg (0.095 mmoles) of the carbapenem 16 in 2 ml anhydrous $CH_2Cl_2$ and ethyl acetate at 0° under a $N_2$ atmosphere was added a mixture of 14.6 mg ($1.26 \times 10^{-5}$ moles) of tetrakis(triphenylphosphine)palladium and 15.6 mg ($5.94 \times 10^{-5}$ moles) of triphenylphosphine, followed by 17.4 μl (0.11 mmoles) of 2-ethylhexanoic acid and 0.218 ml (0.11 mmoles) of a 0.5M potassium 2-ethylhexanoate in EtOAc solution. The resulting mixture was stirred 0.5 hrs at 0° and 3.5 hrs at room temperature under a $N_2$ atmosphere. A light coloured precipitate developed after 30 minutes at room temperature. The reaction slurry was then diluted with EtOAc and the solid separated and washed 2× with $Et_2O$. The solid was then dried under vacuum and purified by reverse phase-PLC ($2 \times 1000\mu$, $20 \times 20$ cm rev. phase silica gel F, eluted at ~5° with 30% THF in $H_2O$). The major UV active product bands were combined and extracted 8 times with $CH_3CN-H_2O$ (4:1). The combined aqueous extracts were washed 3 times with hexanes, filtered through a Gelman Acrodisc-CR 0.45μ filter assembly and concentrated under vacuum. The concentrate was lyophilized to give 15.5 mg of the title compound as a white fluffy solid.

$^1$H—NMR (300 MHz, $D_2O$/THF—$d_8$/TSP) δ1.35 (d, J=6.8 Hz, $CH_3CHCH$), 3.18 (dd, J=9.5, 17.2 Hz, $CH_2CHCH$) 3.46 (dd, J=2.7, 6.1 Hz, $CHCHC=O$), 3.57 (dd, J=8.8, 17.2 Hz, $CH_2CHCH$), 4.26 (m, $CH_3CHOH$), 4.35 (dt, J=2.0, 9.2 Hz, $CHCHCH_2$), 6.88 (d, J=7.9 Hz, pyridine-H3 and H5), 7.56 (m, 2 naphthyl-H), 7.87 (d, J=6.7 Hz, naphthyl-H), 7.95 (m, 3 napht-hyl-H), 8.20 ppm (d, J=6.9 Hz, pyridine-H2 and H6); UV($H_2O$): $\lambda_{max}$=274, 319 nm.

EXAMPLES 17-33

Operating as described in the previous examples, the following compounds were analogously prepared:

| | EXAMPLE NO. | | | $\lambda_{max}^{H2O}$ |
|---|---|---|---|---|
| [structure with $CO_2M$ and $R^a$] | 17 | $R^a =$ | [3-aminopyridinium with ethyl] | M = (−) 286 nm 319 nm |
| | 18 | $R^a =$ | [pyridinium with ethyl and SMe] | M = (−) 287 nm 319 nm |
| | 19 | $R^a =$ | [pyridinium with ethyl and $CO_2^-$] | M = K 275 nm 319 nm |
| | 20 | $R^a =$ | [2-aminopyridinium with ethyl] | M = (−) 310 nm 286 nm |

-continued

| EXAMPLE NO. | | | | $\lambda_{max}^{H2O}$ |
|---|---|---|---|---|
| 21 | $R^a =$ | 2-(ethylamino)pyridine | M = K | 318 nm
273 nm |
| 22 | $R^a =$ | 1-ethyl-4-(2-sulfonatoethyl)pyridinium | M = K | 319 nm |
| 23 | $R^a =$ | 1-ethylquinolinium | M = (−) | 316 nm |
| 24 | $R^a =$ | 2-ethylisoquinolinium | M = (−) | 320 nm |
| 25 | $R^a =$ | 1-ethylpyridinium | M = (−) | 319 nm |
| 26 | $R^a =$ | 4-amino-1-ethylpyridinium | M = (−) | 316 nm |
| 27 | $R^a =$ | 2-amino-1-ethylpyridinium | M = (−) | 316 nm
283 nm |
| 28 | $R^a =$ | 2-(ethylamino)pyridine | M = K | 316 nm |
| 29 | $R^a =$ | 4-amino-1-ethylpyridinium | M = (−) | 318 nm |

| EXAMPLE NO. | | | $\lambda_{max}^{H_2O}$ |
|---|---|---|---|
| 30 | $R^a =$ 4-amino-1-ethylpyridinium | M = (−) | 316 nm |
| 31 | $R^a =$ 4-amino-1-ethylpyridinium | M = (−) | 318 nm |
| 32 | $R^a =$ 2-(ethylamino)pyridine | M = K | 316 nm, 286 nm |
| 33 | $R^a =$ 2-amino-1-ethylpyridinium | M = (−) | 307 nm, 286 nm |

EXAMPLE 34

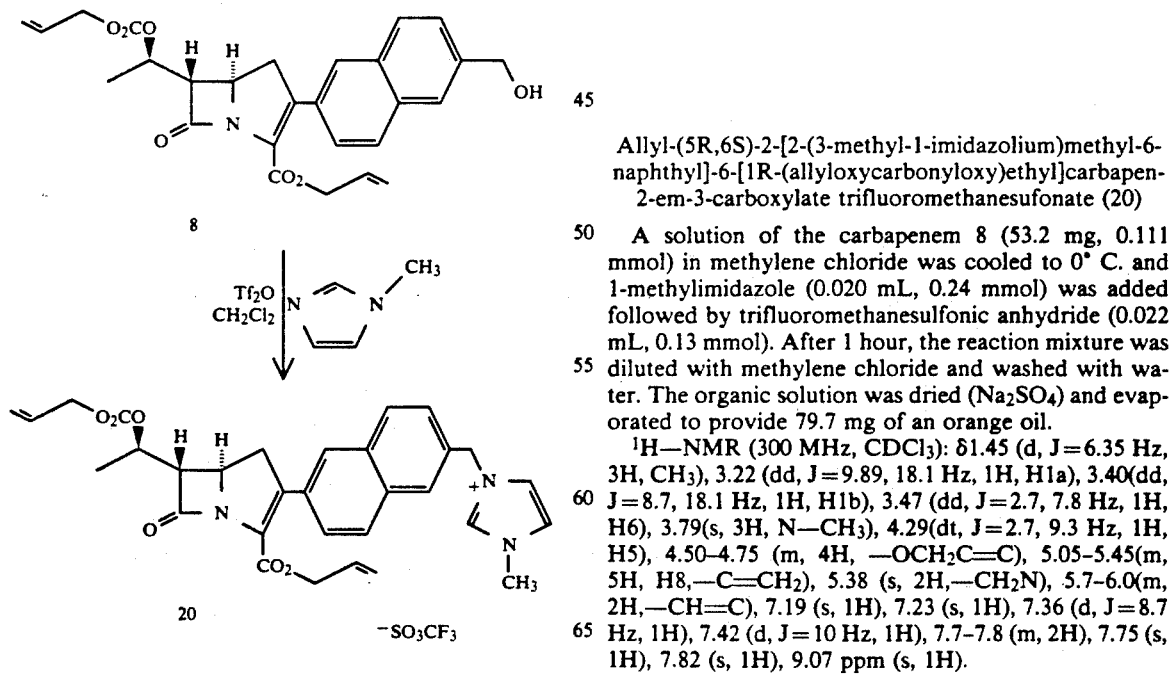

Allyl-(5R,6S)-2-[2-(3-methyl-1-imidazolium)methyl-6-naphthyl]-6-[1R-(allyloxycarbonyloxy)ethyl]carbapen-2-em-3-carboxylate trifluoromethanesufonate (20)

A solution of the carbapenem 8 (53.2 mg, 0.111 mmol) in methylene chloride was cooled to 0° C. and 1-methylimidazole (0.020 mL, 0.24 mmol) was added followed by trifluoromethanesulfonic anhydride (0.022 mL, 0.13 mmol). After 1 hour, the reaction mixture was diluted with methylene chloride and washed with water. The organic solution was dried (Na$_2$SO$_4$) and evaporated to provide 79.7 mg of an orange oil.

$^1$H—NMR (300 MHz, CDCl$_3$): δ1.45 (d, J=6.35 Hz, 3H, CH$_3$), 3.22 (dd, J=9.89, 18.1 Hz, 1H, H1a), 3.40(dd, J=8.7, 18.1 Hz, 1H, H1b), 3.47 (dd, J=2.7, 7.8 Hz, 1H, H6), 3.79(s, 3H, N—CH$_3$), 4.29(dt, J=2.7, 9.3 Hz, 1H, H5), 4.50–4.75 (m, 4H, —OCH$_2$C=C), 5.05–5.45(m, 5H, H8,—C=CH$_2$), 5.38 (s, 2H,—CH$_2$N), 5.7–6.0(m, 2H,—CH=C), 7.19 (s, 1H), 7.23 (s, 1H), 7.36 (d, J=8.7 Hz, 1H), 7.42 (d, J=10 Hz, 1H), 7.7–7.8 (m, 2H), 7.75 (s, 1H), 7.82 (s, 1H), 9.07 ppm (s, 1H).

EXAMPLE 35

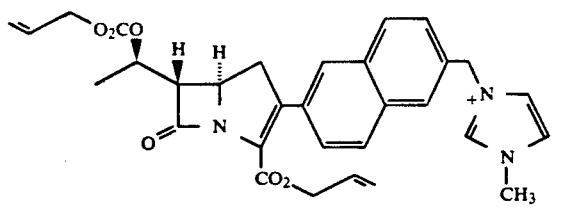

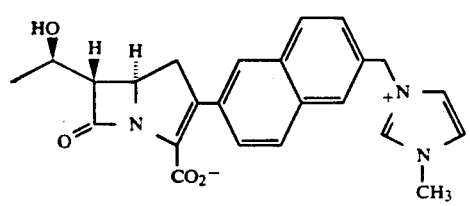

(5R,6S)-2-[2-(3-methyl-1-imidazolium)methyl-6-naphthyl]-6-(1R-hydroxyethyl)-carbapen-2-em-3-carboxylate (21)

In an analogous manner to that described in Example 12, carbapenem 20 (79.7 mg) was de-allylated to yield the title compound (11.7 mg, 25%) as a yellow lyophilized solid.

$^1$H—NMR(300 MHz, 2:1 D$_2$O/CD$_3$CN): δ1.65 (d, J=6.2 Hz, 3H, CH$_3$), 3.50 (dd, J=9.8, 16.5 Hz, 1H, H1a), 3.75-3.95 (m, 2H, H1b, H6), 4.20 (s, 3H, —NCH$_3$), 4.5-4.7 (m, 2H, H5, H8), 5.85 (s, 2H, —CH$_2$N), 7.80 (s, 1H), 7.84 (s, 1H), 7.75-7.85 (d, 1H, obscured), 7.98 (d, J=8.7 Hz, 1H), 8.20 (s, 1H), 8.24 (s, 1H), 8.20-8.25 (d, 1H, obscured), 8.29 ppm (d, J=8.4 Hz, 1H).

IR(KBr): 1755 (β-lactam), 1595 cm$^{-1}$(carboxylate).

UV(H$_2$O): λ$_{max}$=319 nm; ε=9,700.

EXAMPLE 36

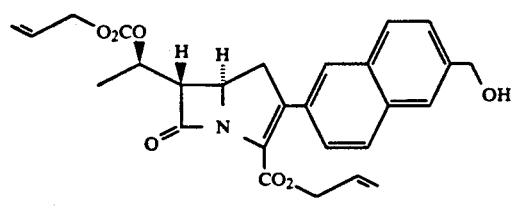

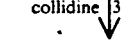

1. Tf$_2$O, CH$_2$Cl$_2$ collidine  2. 3-aminopyridine  3. NH$_4$Cl/H$_2$O

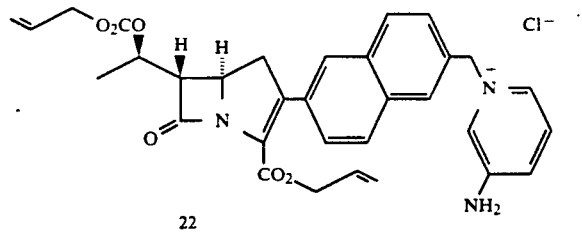

Allyl-(5R,6S)-2-[2-(3-aminopyridinium)methyl-6-naphthyl]-6-[1R-(allyloxycarbonyloxy)ethyl]carbapen-2-em-3-carboxylate chloride (22)

A solution of the carbapenem 8 (66.2 mg, 0.139 mmol) in CH$_2$Cl$_2$ was cooled to −70° C. and collidine (0.022 mL, 0.17 mmol) was added followed by trifluoromethanesulfonic anhydride (0.026 mL, 0.15 mmol). The pale orange solution was stirred at −70° C. for 30 minutes and then a solution of 3-aminopyridine in CH$_2$Cl$_2$ (4.1M, 0.074 mL, 0.30 mmol) was added dropwise. The reaction mixture was allowed to warm gradually to −20° C. during 35 minutes and was then hydrolyzed with sat. NH$_4$Cl—H$_2$O (1:1). The reaction mixture was partitioned between EtOAc and sat. NH$_4$Cl—H$_2$O (1:1) and the organic phase was washed with water and brine. Drying (Na$_2$SO$_4$) and evaporation gave 84 mg of a brown oil. This material was dissolved in CH$_2$Cl$_2$ (1 mL) and pipetted into ethyl ether (2 mL) in a centrifuge tube. The resulting solid was isolated by centrifugation and dried in vacuo to yield 72 mg (88%) of the pyridinium salt.

$^1$H—NMR (300 MHz, CDCl$_3$): δ1.46 (d, J=6.16 Hz, 3H, CH$_3$), 3.15-3.45 (m, 2H, H1), 3.46 (dd, J=2.5, 8.0 Hz, 1H, H6), 4.3 (br t, J=9 Hz, 1H, H5), 4.4-4.8 (m, 4H, —OCH$_2$C=C), 5.0-5.5 (m, 5H, H8, —C=CH$_2$), 5.7-6.0 (m, 4H,—CH=C, —CH$_2$N), 7.2-7.9 (m, 9H), 8.45 ppm (broad s, 1H).

EXAMPLE 37

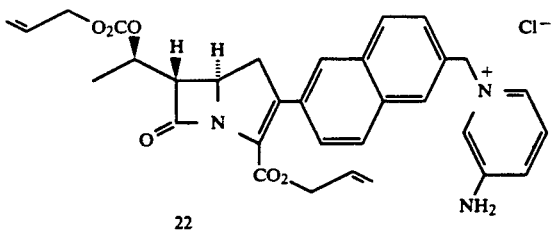

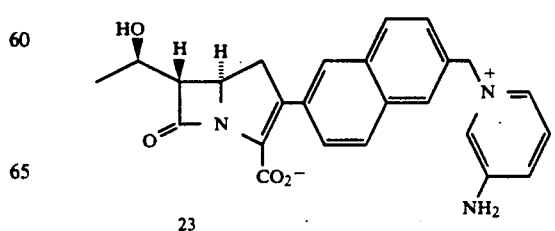

(5R,6S)-2-[2-(3-Aminopyridinium)methyl-6-naphthyl]-6-(1R-hydroxyethyl)-carbapen-2-em-3-carboxylate (23)

In an analogous manner to that described in Example 12, carbapenem 22 (72 mg, 0.12 mmol) was de-allylated to yield the title compound (12.5 mg, 24%) as a pale yellow lyophilized solid $^1$H-NMR (300 MHz, 2:1 D$_2$O/CD$_3$CN): δ1.64 (d, J=6.2 Hz, 3H, CH$_3$), 3.49 (dd, J=9.8, 16.5 Hz, 1H, H1a), 3.75-3.95 (m, 2H, H1b, H6), 4.5-4.7 (m, 2H, H5, H8), 6.05 (s, 2H, —CH$_2$N), 7.8 (d, J=7.7 Hz, 1H), 7.9-8.05 (m, 3H), 8.15-8.35 (m, 4H), 8.4-8.5 ppm (m, 2H).

IR(KBr): 1750 (β-lactam), 1585 cm$^{-1}$(carboxylate).
UV(H$_2$O): λ$_{max}$=313 nm; ε=15,700.

EXAMPLE 38

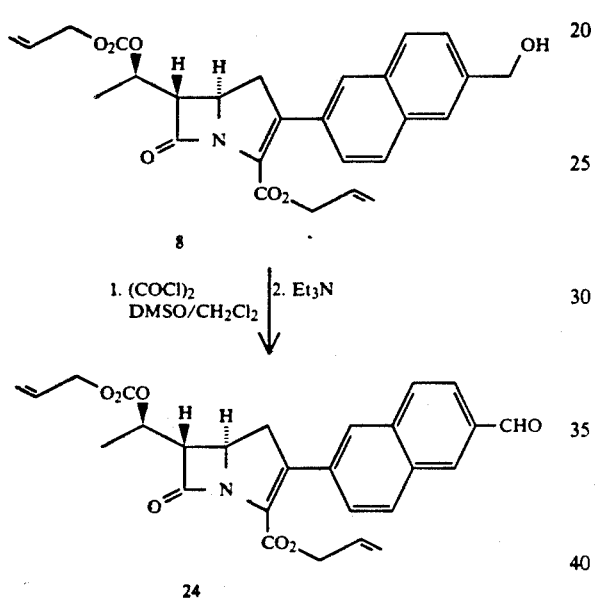

Allyl-(5R,6S)-2-(2-formyl-6-naphthyl)-6-[1R-(allyloxycarbonyloxy)ethyl]-carbapen-2-em-3-carboxylate (24)

To a stirring solution of oxalyl chloride (0.023 mL, 0.24 mmol) in 1.5 mL of methylene chloride at −70° C. was added neat dimethylsulfoxide (0.023 mL, 0.32 mmol). After 5 minutes., a solution of the alcohol 8 (113 mg, 0.237 mmol) in 0.5 mL of methylene chloride was added dropwise. The reaction mixture was stirred at −70° C. for 15 minutes and then triethylamine (0.091 mL, 0.65 mmol) was added. The temperature was maintained at −70° C. for 5 minutes more, and was then allowed to warm gradually to 0° C. during 2 hours. The reaction mixture was quenched with pH 7 phosphate buffer and was then diluted with ethyl acetate and washed successively with pH 7 phosphate buffer, water (2×) and brine. Drying (MgSO$_4$) and evaporation gave 105 mg (93%) of the title aldehyde as an oil which required no purification.

$^1$H-NMR (300 MHz, CDCl$_3$): δ1.51 (d, J=5.61 Hz, 3H, CH$_3$), 3.25-3.50 (m, 3H, H6, H1), 4.36 (dt, J=2.75, 9.4 Hz, 1H, H5), 4.55-4.8 (m, 4H, —OCH$_2$C≡C), 5.1-5.4 (m, 5H, H8, —C≡CH$_2$), 5.75-6.0 (m, 2H, —CH≡C), 7.56 (d, J=8.61 Hz, 1H, ArH), 7.8-8.0 (m, 4H, ArH), 8.32 (s, 1H, ArH), 10.16 ppm (s, 1H, CHO).

EXAMPLE 39

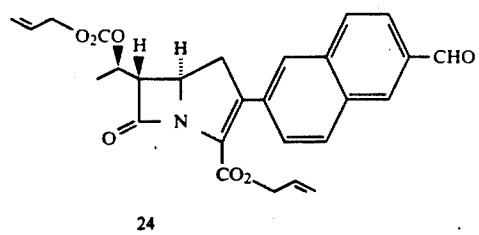

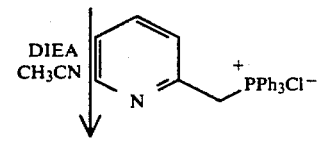

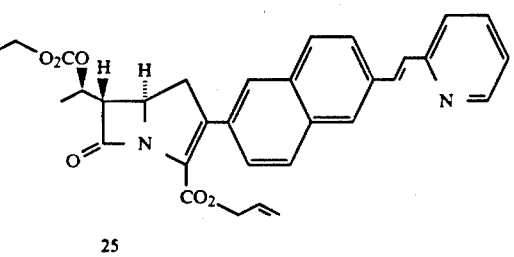

Allyl-(5R,6S)-2-{6-[E-2-(2-pyridyl)vinyl]-2-naphthyl}-6-[1R-(allyloxycarbonyloxy)ethyl]carbapen-2-em-3-carboxylate (25)

To a solution of the aldehyde 24 (105 mg, 0.221 mmol) in 2.5 mL of acetonitrile was added (2-picolyl)-triphenylphosphonium iodide (129 mg, 0.34 mmol) followed by diisopropylethylamine (0.050 mL, 0.29 mmol). The reaction mixture was stirred at room temperature for 5 hours and was then diluted with ethyl acetate and washed with sat. NH$_4$Cl, sat. NaHCO$_3$, and brine. Drying (MgSO$_4$), evaporation, and purification by preparative TLC on silica gel yielded 58 mg (48%) of the title compound as an oil.

$^1$H-NMR (300 MHz, CDCl$_3$): δ1.51 (d, J=6.29 Hz, 3H, CH$_3$), 3.25-3.5 (m, 2H, H1), 3.45 (dd, J=8.4, 2.8 Hz, 1H, H6), 4.33 (dt, J=2.8, 9.3 Hz, 1H, H5), 4.55-4.8 (m, 4H, —OCH$_2$C≡C), 5.1-5.5 (m, 5H, H8, —C≡CH$_2$), 5.75-6.0 (m, 2H, —CH≡C), 7.15-7.90 (m, 11H, ArH, CH≡CH), 8.63 ppm (d, J=4.82 Hz, 1H, ArH).

IR (CHCl$_3$): 1780 (β-lactam), 1745 (carbonate), 1725 (ester), 1590 cm$^{-1}$ (olefin).

FAB-MS: m/e=551 (M+H).

EXAMPLE 40

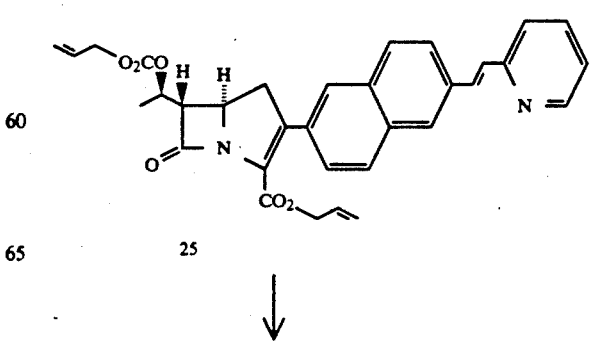

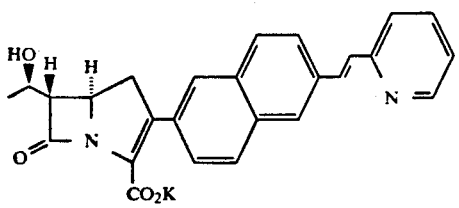

26

Potassium (5R,6S)-2-{6-[E-2-(2-pyridyl)vinyl]-2-naphthyl}-6-(1R-hydroxyethyl)-carbapen-2-em-3-carboxylate (26)

To solution of carbapenem 25 (29 mg, 0.053 mmol) in ethyl acetate (1 mL)-methylene chloride (1 mL) were added in sequence triphenylphosphine (4 mg, 0.016 mmol), 2-ethylhexanoic acid (0.0080 mL, 0.053 mmol), potassium 2-ethylhexanoate (0.50M solution in EtOAc, 0.105 mL, 0.053 mmol) and tetrakis(triphenylphosphine)palladium (6 mg, 0.005 mmol). The reaction mixture was stirred at room temperature for 2 hours and was then pipetted into a centrifuge tube containing ethyl acetate. The resulting solid was isolated by centrifugation, washing twice with ethyl acetate. Purification by reverse phase preparative TLC (4:1 H2O/THF) yielded 7.0 mg (28%) of the title compound as a white lyophilized solid.

$^1$H-NMR (300 MHz, d$_8$-THF/D$_2$O): δ1.4 (d, J=6 Hz, 3H, CH$_3$), 3.1–3.25 (m, 1H, H1a), 3.5–3.65 (m, 2H, H1b, H6), 4.25–4.45 (m, 2H, H5, H8), 7.3–8.1 (m, 11H, ArH, CH=CH), 8.6 ppm (bs, 1H, ArH).

IR(KBr): 1750 (β-lactam), 1590 cm$^{-1}$ (carboxylate).
UV(H$_2$O): λ$_{max}$=349 nm; ε=28,500.

EXAMPLE 41

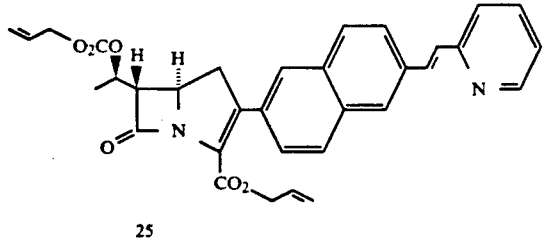

25

CF$_3$SO$_3$CH$_3$ | CH$_2$Cl$_2$

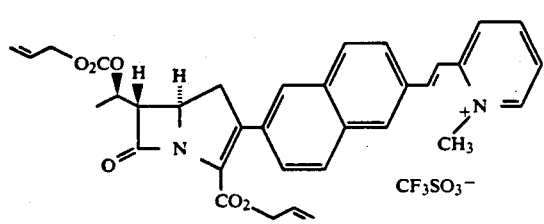

27

Allyl-(5R,6S)-2-{6-[E-2-(N-methyl-2-pyridinium)vinyl]-2-naphthyl}-6-[1R-(allyloxycarbonyloxy)ethyl]carbapen-2-em-carboxylate trifluoromethanesulfonate (27)

To a solution of the carbapenem 25 (28 mg, 0.051 mmol) in 1.5 mL of methylene chloride was added methyl trifluoromethanesulfonate (6.0 μL 0.53 mmol). After 6 hours at room temperature, the solvent was evaporated in vacuo leaving the title compound as an orange solid.

$^1$H-NMR (300 MHz, CDCl$_3$): δ1.49 (d, J=6.11 Hz, 3H, CH$_3$), 3.15–3.55 (m, 3H, H1, H6), 4.15 (s, 3H, N—CH$_3$), 4.33 (br t, J=9.3 Hz, 1H, H5), 4.5–4.85 (m, 4H, —OCH$_2$C=C), 5.1–5.45 (m, 5H, H8, —C=CH$_2$), 5.8–6.0 (m, 2H, —CH=C), 7.2–8.2 ppm (m, 12H, ArH, CH=CH).

IR (CHCl$_3$): 1780 (β-lactam), 1745 (carbonate, 1725 (ester), 1615 cm$^{-1}$ (olefin).

EXAMPLE 42

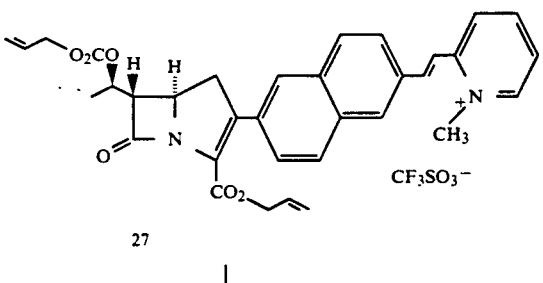

27

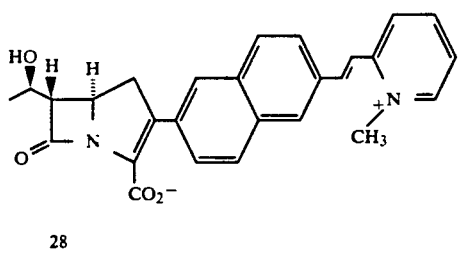

28

(5R,6S)-2-{6-[E-2-(N-Methyl-2-pyridinium)vinyl]-2-naphthyl}-6-(1R-hydroxyethyl)-carbapen-2-em-3-carboxylate (28)

Carbapenem 27 was de-allylated in a manner analogous to that described in Example 12 to give the title compound (7.0 mg, 31% overall) as a yellow lyophilized solid.

IR (KBr): 1750 (β-lactam), 1610 cm$^{-1}$ (carboxylate).
UV (H$_2$O): λ$_{max}$=368 nm (ε=24,000).

EXAMPLES 43–46

Operating as described in the preceding examples, the following compounds were analogously prepared:

| EXAMPLE NO. | | $R^a$ = | | $\lambda_{max}^{H_2O}$ |
|---|---|---|---|---|
| | 43 | (2-propenyl-pyridine) | M = K | 319 nm |
| | 44 | (2-propenyl-quinoline) | M = K | 335 nm |
| | 45 | (N-methyl-2-propenyl-quinolinium) | M = (−) | 390, 315 nm |
| | 46 | (2-propenyl-pyridine) | M = K | 318 nm |

EXAMPLE 47

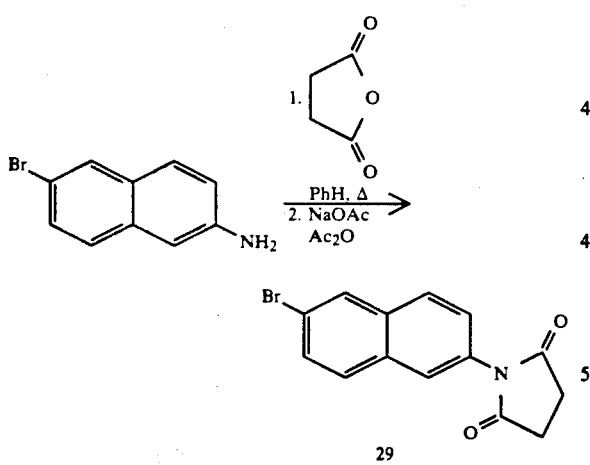

2-Bromo-6-(N-succinimido)-naphthalene (29)

A solution of 2-amino-6-bromonaphthalene (0.565 g, 2.54 mmol) and succinic anhydride (0.508 g, 5.08 mmol) in 13 mL of benzene was refluxed for 1.5 hours. The resulting precipitate was isolated by filtration, washing with additional benzene. After drying in vacuo, 0.780 g of a solid was obtained which was dissolved in 12 mL of acetic anhydride along with sodium acetate (0.595 g, 7.26 mmol) and refluxed for 3 hours. After cooling to room temperature, the reaction mixture was quenched with 3 mL of water and was evaporated to dryness under high vacuum. Purification by flash chromatography through 150 g of silica gel (1:4 EtOAc/CH$_2$Cl$_2$) yielded 0.670 g (86%) of the title compound as a white solid.

$^1$H-NMR (300 MHz, CDCl$_3$): δ2.95 (bs, 4H), 7.41 (dd, J=8.8, 1.9 Hz, 1H), 7.59 (dd, J=8.8, 1.7 Hz, 1H), 7.73 (d, J=8.8 Hz, 1H), 7.79 (s, 1H), 7.84 (d, J=8.8 Hz, 1H), 8.04 ppm (s, 1H).

FAB-MS: m/e=504,506 (M+H).

EXAMPLE 48

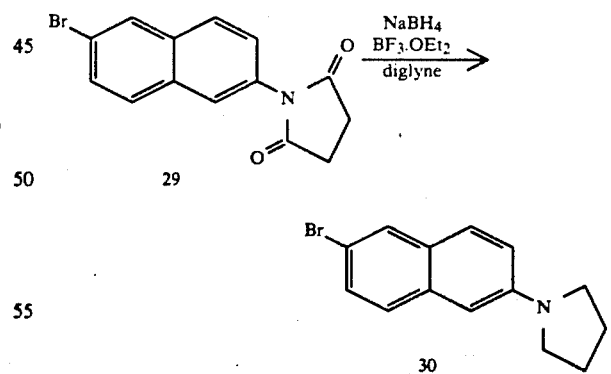

2-Bromo-6-(N-pyrrolidino)naphthalene (30)

To a solution of 2-bromo-6-(N-succinimido)naphthalene 29 (0.670 g, 2.20 mmol) in 7 mL of 2-methoxyethyl ether at 0° C. was added boron trifluoride etherate (0.567 mL, 4.61 mmol) followed by dropwise addition of a solution of sodium borohydride (0.166 g, 4.39 mmol) in 6 mL of 2-methoxyethyl ether. After 1 hour the reaction mixture was carefully hydrolyzed with water followed by saturated NaHCO$_3$ and was then partitioned between methylene chloride and saturated NaHCO₃. The organic phase was dried (MgSO₄) and evaporated to leave a solid which was purified by flash chromatography through 75 g of silica gel (1:4 EtOAc/CH₂Cl₂) to yield 0.540 g (88%) of the title compound as a white solid.

¹H—NMR (300 MHz, CDCl₃): δ2.0–2.1 (m, 4H, —CH₂CH₂—), 3.35–3.45 (m, 4H, —CH₂NCH₂—), 6.73 (bs, 1H), 7.01 (dd, J=9.0, 2.3 Hz, 1H), 7.39 (dd, J=8.8, 2.0 Hz, 1H), 7.50 (d, J=8.8 Hz, 1H), 7.60 (d, J=9.0 Hz, 1H), 7.88 ppm (d, J=1.8 Hz, 1H).

UV(CH₃CN): λmax=252 nm; ε=8,000, 218 nm; ε=20,800.

FAB-MS: m/e=276,278 (M+H).

EXAMPLE 49

(3S,4R)-1-(Allyloxycarbonyltriphenylphosphoranylidene)methyl-3-[1R-(allyloxycarbonyloxy)ethyl]-4-[2-(N-pyrrolidino)-6-naphthylcarbonyl]methylazetidin-2-one (31)

To a mixture of bromide 30 (0.260 g, 0.945 mmol) and magnesium turnings (32 mg, 1.3 mmol) in 3 mL of tetrahydrofuran was added 1,2-dibromoethane (0.010 mL) and the reaction mixture was sonicated briefly in an ultrasonic bath to initiate the Grignard formation. The mixture was heated at 50° C. for 10 minutes and was then stirred at room temperature for 3 hours. The Grignard solution thus prepared was added dropwise to a solution of 0.539 g (0.759 mmol) of (3S,4R)-1-(allyloxycarbonyltriphenylphosphorylidene)methyl-3-[1R-(allyloxycarbonyloxy)-ethyl]-4-[(2-pyridylthio)carbonyl]-methyl-azetidin-2-one, 3, in 8 mL of tetrahydrofuran at 0° C. After 2 hours, the reaction mixture was hydrolyzed with saturated NH₄Cl solution, diluted with a large volume of ethyl acetate, and washed successively with saturated NH₄Cl, 1N NaOH, H₂O, and brine. Drying (MgSO₄) and evaporation gave a yellow oil which was separated by flash chromatography through 75 g of silica gel (7:3 EtOAc/hexane) to yield 0.411 g (68%) of the title compound as a yellow-green oil.

¹H—NMR (300 MHz, CDCl₃): δ1.16 (d, J=6.11 Hz, 3H, CH₃), 2.0–2.15 (m, 4H, —CH₂CH₂—), 3.35–3.50 ppm (m, 4H, —CH₂—N—CH₂—).

IR (CHCl₃): 1745 (β-lactam, carbonate), 1665 (ketone), 1620 cm⁻¹ (ylide).

FAB-MS: m/e=795 (M+H).

EXAMPLE 50

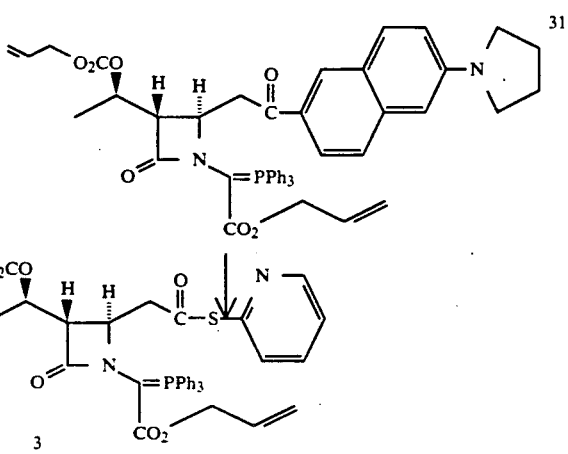

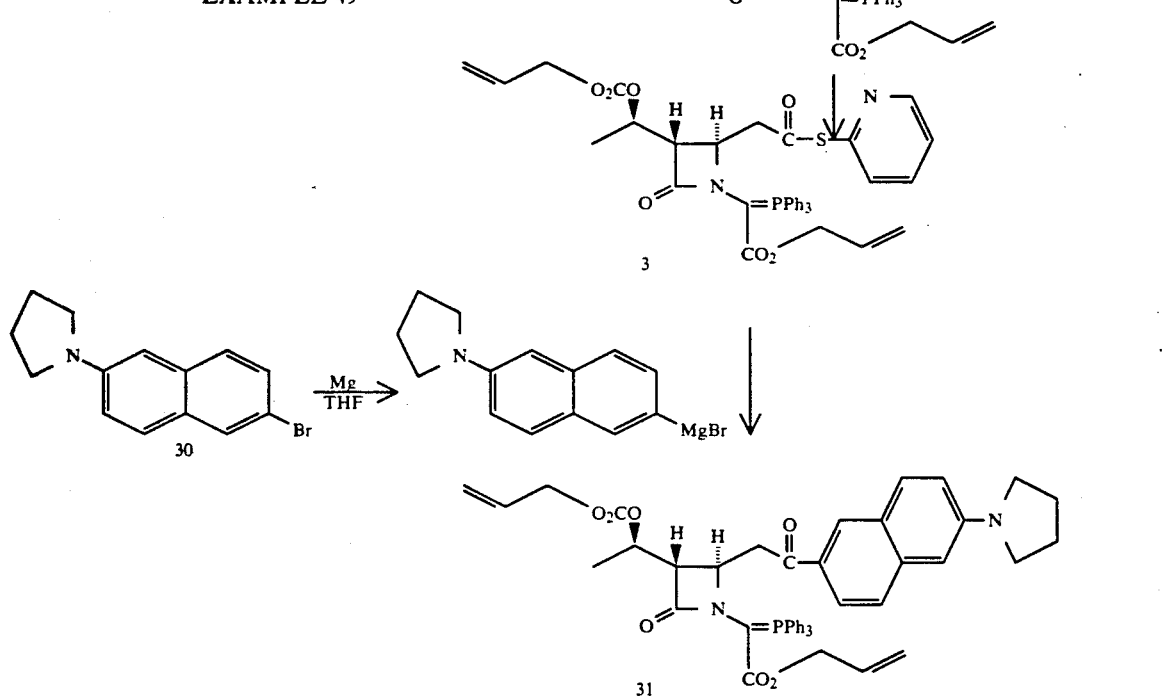

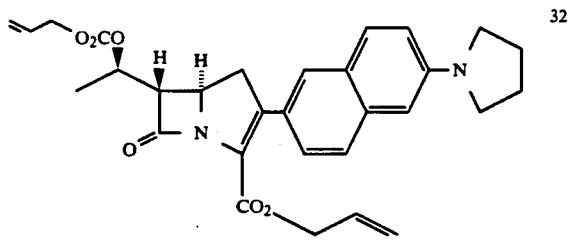

Allyl-(5R,6S)-2-[2-(N-pyrrolidino)-6-naphthyl]-6-[1R-(allyloxycarbonyloxy)ethyl]-carbapen-2-em-3-carboxylate (32)

The phosphorane 31 prepared in the preceding example (0.411 g, 0.518 mmol) was dissolved in 18 mL of p-xylene along with several crystals of p-hydroquinone and the solution was heated to reflux (138° C.). After 3 hours the solution was cooled to room temperature, the solvent was evaporated in vacuo, and the residue was purified by flash chromatography through 30 g of silica gel (3:2 EtOAc/hexane) to yield 0.177 g (66%) of the title compound as a yellow-green foam.

¹H—NMR (300 MHz, CDCl₃): δ1.50 (d, J=6.34 Hz, 3H, CH₃), 2.0-2.1 (m, 4H, —CH₂CH₂—), 3.25-3.50 (m, 7H, H1, H6, —CH₂NCH₂—), 4.27 (dt, J=2.7, 9.3 Hz, 1H, H5), 4.6-4.8 (m, 4H, —OCH₂C=C), 5.1-5.4 (m, 5H, H8, —C=CH₂), 5.8-6.0 (m, 2H, —CH=C), 6.7-7.7 ppm (m, 6H, ArH).

IR (CHCl₃): 1780 (β-lactam), 1745 (carbonate), 1720 (ester), 1625 cm⁻¹ (C=C).

UV (CH₃CN): λ$_{max}$=387, 246 nm.

FAB-MS: m/e=517 (M+H).

EXAMPLE 51

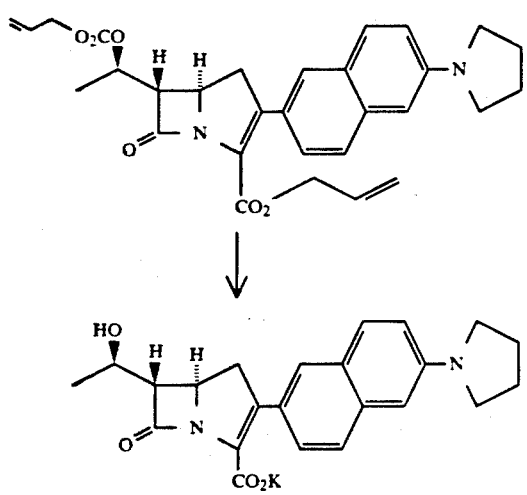

Potassium (5R,6S)-2-[2-(N-pyrrolidino)-6-naphthyl]-6-(1R-hydroxyethyl)-carbapen-2-em-3-carboxylate (33)

To a solution of the carbapenem 32 (35 mg, 0.068 mmol) in ethyl acetate (1 mL) - methylene chloride (1 mL) were added sequentially triphenylphosphine (5mg, 0.02 mmol), 2-ethylhexanoic acid (0.012 mL, 0.080 mmol), potassium 2-ethylhexanoate (0.5M solution in EtOAc, 0.17 mL, 0.085 mmol), and tetrakis(triphenylphosphine)palladium (8 mg, 0.007 mmol). The reaction mixture was stirred at room temperature for 1.5 hours and was then pipetted into a centrifuge tube containing ethyl acetate (2 mL). The precipitate was isolated by centrifugation washing once with ethyl ether. Separation by reverse phase preparative TLC (4:1 H₂O/THF) yielded 8.0 mg (30%) of the title compound as an off-white lyophilized solid.

¹H—NMR (300 MHz, D₂O): δ1.63 (d, J=6.41 Hz, 3H, CH₃), 2.30-2.45 (m, 4H, —CH₂CH₂—), 3.46 (dd, J=9.9, 16.5 Hz, 1H, H1a), 3.65-3.85 (m, 6H, H1b, H6, —CH₂NCH₂—), 4.50-4.65 (m, 2H, H6, H8), 7.18 (s, 1H), 7.43 (dd, J=9.1, 1.9 Hz, 1H), 7.80 (d, J=8.7 Hz, 1H), 7.93 (d, J=8.7 Hz, 1H), 8.01 (s, 1H), 8.07 ppm (d, J=9.1 Hz, 1H).

IR(KBr): 1750 (β-lactam), 1625 (C=C), 1600 cm⁻¹ (carboxylate).

UV (H₂O): λ$_{max}$=342 nm (ε=15,000), 246 nm.

EXAMPLE 52

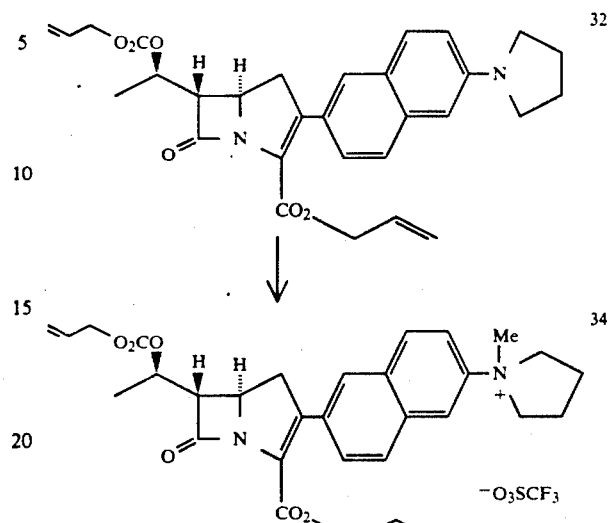

Allyl-(5R-6S)-2-[2-(N-methyl-N-pyrrolidinium)-6-naphthyl]-6-[1R-(allyloxycarbonyloxy)ethyl]carbapen-2-em-3-carboxylate trifluoromethane sulfonate (34)

To a solution of carbapenem 32 (0.177 g, 0.343 mmol) in 6 mL of methylene chloride was added methyl trifluoromethanesulfonate (0.043 mL, 0.38 mmol). After stirring at room temperature for 6 hours the volatiles were evaporated in vacuo to leave the title compound as a foam.

¹H—NMR (300 MHz, CDCl₃): δ1.47 (d, J=6.35 Hz, 3H, CH₃), 2.15-2.40 (m, 4H, —CH₂CH₂—), 3.2-3.55 (m, 2H, H1), 3.42 (s, 3H, N—CH₃), 3.52 (dd, J=7.8, 2.7 Hz, 1H, H6), 3.90-4.05, 4.30-4.45 (m, 4H, —CH₂—N—CH₂—), 4.30-4.45 (H5, obscured), 4.5-4.8 (m, 4H, —OCH₂C=C), 5.1-5.4 (m, 5H, H8, —C=CH₂), 5.75-6.0 (m, 2H, —CH=C), 7.53 (d, J=8.7 Hz, 1H), 7.72 (d, J=9.2 Hz, 1H), 7.84 (s, 1H), 7.92 (d, J=8.9 Hz, 2H), 8.17 ppm (s, 1H).

IR (CHCl₃): 1780 (β-lactam), 1745 (carbonate), 1725 cm⁻¹ (ester)

EXAMPLE 53

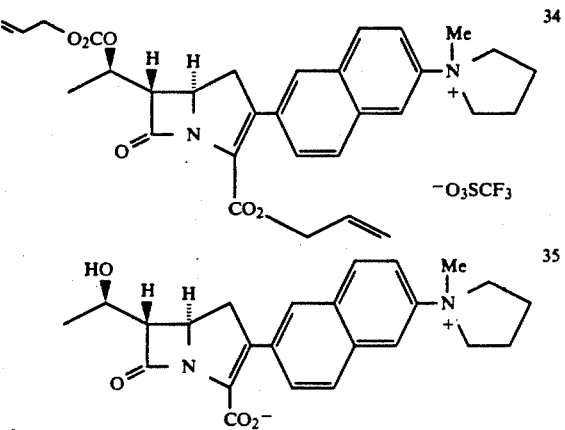

(5R,6S)-2-[2-(N-methyl-N-pyrrolidinium)-6-naphthyl]-6-(1R-hydroxyethyl)-carbapen-2-em-3-carboxylate (35)

Carbapenem 34, prepared in the preceding example, was de-allylated in a manner analogous to that described in Example 51 to yield 39 mg (28% for two steps) of the title compound as a yellow lyophilized solid.

$^1$H—NMR (300 MHz, D$_2$O): δ1.35 (d, J=6.41 Hz, 3H, CH$_3$), 2.3–2.5 (m, 4H, —CH$_2$CH$_2$—), 3.13 (dd, J=9.8, 16.7 Hz, 1H, H1a), 3.45–3.60 (m, 2H, H1b, H6), 3.52 (s, 3H, NCH$_3$), 4.05–4.20, 4.25–4.40 (m, 4H, —CH$_2$—N—CH$_2$), 4.25–4.40 (m, 2H, H5, H8), 7.59 (dd, J=8.9, 2.7 Hz, 1H), 7.7 (d, 1H, partially obscured), 7.83 (s, 1H), 7.92 (d, J=8.9 Hz, 1H), 8.07 (d, J=9.3 Hz, 1H), 8.22 ppm (d, J=2.4 Hz, 1H).

IR (KBr): 1755 (β-lactam), 1600 cm$^{-1}$ (carboxylate).
UV (H$_2$O): λ$_{max}$=318 nm (ε=13,500), 276 nm.
FAB-MS: m/e=407 (M+H).

EXAMPLE 54

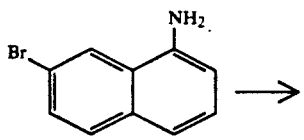

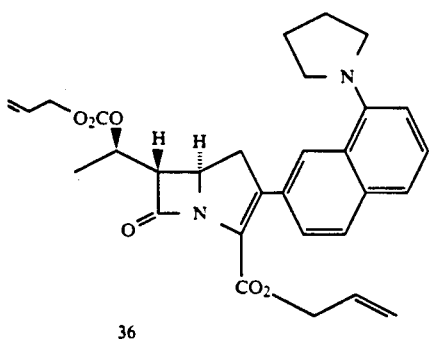

Allyl-(5R,6S)-2-[1-(N-pyrrolidino)-7-naphthyl]-6-[1R-(allyloxycarbonyloxy)ethyl]-carbapen-2-em-3-carboxylate (36)

In a manner analogous to that described in Examples 47–50, but starting with 1-amino-7-bromonaphthalene [H. H. Hodgson and R. E. Dean, H. Chem. Soc. 818 (1950)], the title compound was obtained as an orange oil.

$^1$H—NMR (300 MHz, CDCl$_3$)): δ1.51 (d, J=6.3 Hz, 3H, CH$_3$), 1.95–2.10 (m, 4H, —CH$_2$CH$_2$—), 3.25–3.40 (m, 6H, H1, —CH$_2$NCH$_2$—), 3.45 (dd, J=8.5, 2.8 Hz, 1H, H6), 4.31 (dt, J=2.8, 9.3 Hz, 1H, H5), 4.6–4.8 (m, 4H, —OCH$_2$C=C), 5.1–5.4 (m, 5H, H8, —C=CH$_2$), 5.8–6.0 (m, 2H, —CH=C), 6.9–7.0 (m, 1H), 7.3–7.5 (m, 3H), 7.74 (d, J=8.7 Hz, 1H), 8.20 ppm (s, 1H).

IR (CHCl$_3$): 1780 (β-lactam), 1745 (carbonate), 1725 cm$^{-1}$ (ester).
UV (CH$_3$CN): λ$_{max}$=307 nm.
FAB-MS: m/e=517 (M+H).

EXAMPLE 55

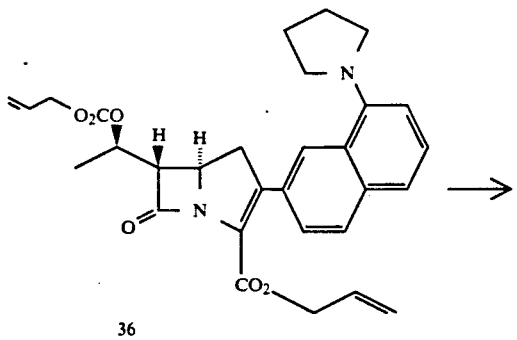

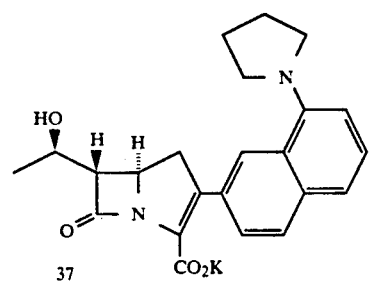

Potassium(5R,6S)-2-[1-(N-pyrrolidino)-7-naphthyl]-6-(1R-hydroxyethyl)-carbapen-2-em-3-carboxylate (37)

Carbapenem 36 (60 mg, 0.12 mmol) was de-allylated in a manner analogous to that described in Example 51 to yield 14.8 mg (30%) of the title compound as a lyophilized solid.

IR (KBr): 1750 (β-lactam), 1590 cm$^{-1}$ (carboxylate).
UV (H$_2$O): λ$_{max}$=295 nm; ε=7,800.

EXAMPLE 56

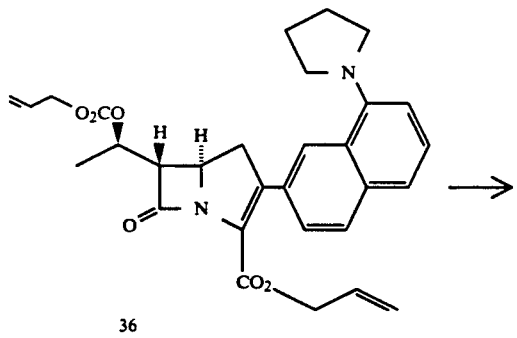

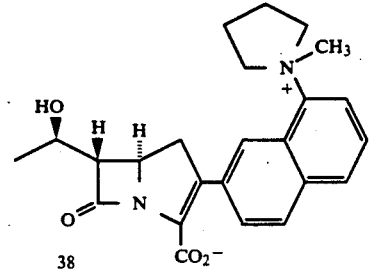

(5R,6S)-2-[1-(N-methyl-N-pyrrolidinium)-7-naphthyl]-6-(1R-hydroxyethyl)-carbapen-2-em-3-carboxylate (38)

In a manner analogous to that described in Examples 52-53, the carbapenem 36 (57 mg, 0.11 mmol) gave the title compound (18 mg, 40%) as an off-white lyophilized solid.

$^1$H—NMR (300 MHz, D$_2$O): δ1.33 (d, J=6.47 Hz, 3H, CH$_3$), 2.20-2.55 (m, 4H, —CH$_2$CH$_2$—), 3.18 (dd, J=9.7, 16.2 Hz 1H, H1a), 3.25-3.6 (m, 2H, H1b, H6), 3.73 (s, 3H, NCH$_3$), 4.2-4.5 (m, 6H, H5, H8, —CH$_2$NCH$_2$—), 7.5-7.6 (m, 2H), 7.95 (d, J=8.5 Hz, 1H), 8.0-8.1 (m, 2H), 8.19 ppm (s, 1H).

IR (KBr): 1755 (β-lactam), 1595 cm$^{-1}$ (carboxylate).
UV (H$_2$O): λ$_{max}$=320 nm; ε=8,900, 280 nm; ε=11,000.

What is claimed is:

1. A compound of the formula:

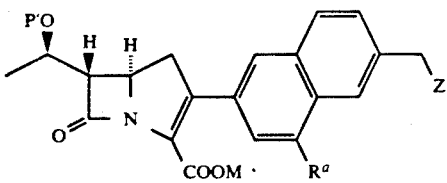

wherein

P' is a removable protecting group for hydroxy;
M is a removable protecting group for carboxy;
R$^a$ is selected from the group consisting of H, Cl, Br, I, SCH$_3$, CN, CHO, SOCH$_3$, SO$_2$CH$_3$, CO$_2$M, CONH$_2$, OP' and CH$_2$OP'; and
Z is an effective leaving group selected from the group consisting of alkylsulfonyloxy, substituted alkylsulfonyloxy, arylsulfonyloxy, substituted arylsulfonyloxy, fluorosulfonyloxy and halogen.

2. The compound of claim 1 wherein M is selected from the group consisting of benzhydryl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, o-nitrobenzyl p-methoxyphenyl, 4-pyridylmethyl and t-butyl.

3. The compound of claim 1 wherein P' is selected from the group consisting of t-butylmethoxyphenylsilyl, t-butoxydiphenylsilyl, trimethylsilyl, triethylsilyl, t-butyldimethylsilyl, o-nitrobenzyloxycarbonyl, p-nitrobenzyloxycarbonyl, benzyoxylcarbonyl, t-butyloxycarbonyl 2,2,2-trichloroethyloxycarbonyl and allyloxycarbonyl.

4. The compound of claim 1 wherein Z is selected from the group consisting of methanesulfonyloxy, trifluoromethanesulfonyloxy, fluorosulfonyloxy, p-toluenesulfonyloxy, 2,4,6-triisopropylbenzenesulfonyloxy, p-bromobenzenesulfonyloxy, p-nitrobenzenesulfonyloxy, bromo and iodo.

* * * * *